(12) United States Patent
Cost

(10) Patent No.: US 10,179,918 B2
(45) Date of Patent: Jan. 15, 2019

(54) METHODS AND COMPOSITIONS FOR INCREASING TRANSGENE ACTIVITY

(71) Applicant: Sangamo BioSciences, Inc., Richmond, CA (US)

(72) Inventor: Gregory J. Cost, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 69 days.

(21) Appl. No.: 15/141,333

(22) Filed: Apr. 28, 2016

(65) Prior Publication Data

US 2016/0326548 A1 Nov. 10, 2016

Related U.S. Application Data

(60) Provisional application No. 62/158,277, filed on May 7, 2015.

(51) Int. Cl.
*C12N 15/10* (2006.01)
*C12N 15/86* (2006.01)
*C12N 15/85* (2006.01)

(52) U.S. Cl.
CPC ............. *C12N 15/86* (2013.01); *C12N 15/85* (2013.01); *C12N 2730/10143* (2013.01); *C12N 2740/16043* (2013.01); *C12N 2740/16045* (2013.01); *C12N 2830/48* (2013.01); *C12N 2840/105* (2013.01); *C12N 2840/60* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo | |
| 6,013,453 A | 1/2000 | Choo | |
| 6,136,597 A | 10/2000 | Hope et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,284,469 B1 | 9/2001 | Hope et al. | |
| 6,287,814 B1 | 9/2001 | Hope et al. | |
| 6,312,912 B1 | 11/2001 | Hope et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,511,808 B2 | 1/2003 | Wolffe et al. | |
| 6,534,261 B1 | 3/2003 | Cox, III et al. | |
| 6,599,692 B1 | 7/2003 | Case et al. | |
| 6,607,882 B2 | 8/2003 | Cox, III et al. | |
| 6,689,558 B2 | 2/2004 | Case | |
| 6,733,970 B2 | 5/2004 | Choo et al. | |
| 6,746,838 B1 | 6/2004 | Choo et al. | |
| 6,794,136 B1 | 9/2004 | Eisenberg et al. | |
| 6,824,978 B1 | 11/2004 | Cox, III et al. | |
| 6,866,997 B1 | 5/2005 | Choo et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox et al. | |
| 7,153,949 B2 | 12/2006 | Kim et al. | |
| 7,163,824 B2 | 1/2007 | Cox, III et al. | |
| 7,241,573 B2 | 6/2007 | Choo et al. | |
| 7,241,574 B2 | 6/2007 | Choo et al. | |
| 7,253,273 B2 | 8/2007 | Collingwood et al. | |
| 7,262,054 B2 | 8/2007 | Jamieson et al. | |
| 7,297,491 B2 | 11/2007 | Joung et al. | |
| 7,361,635 B2 | 4/2008 | Miller et al. | |
| 7,419,829 B2 * | 9/2008 | Mitrophanous | C12N 9/0071 424/93.1 |
| 7,888,121 B2 | 2/2011 | Umov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,034,598 B2 | 10/2011 | Miller et al. | |
| 8,110,379 B2 | 2/2012 | DeKelver et al. | |
| 8,409,861 B2 | 4/2013 | Guschin et al. | |
| 8,420,782 B2 | 4/2013 | Bonas et al. | |
| 8,586,526 B2 | 11/2013 | Gregory et al. | |
| 8,597,912 B2 | 12/2013 | Collingwood et al. | |
| 8,623,618 B2 | 1/2014 | Doyon et al. | |
| 8,697,359 B1 | 4/2014 | Zhang | |

(Continued)

FOREIGN PATENT DOCUMENTS

GB 2338237 A 12/1999
WO WO 95/19431 A1 7/1995

(Continued)

OTHER PUBLICATIONS

Pelascini et al. In Methods in Mole Biol 2014;1114:181-199, Online Feb. 1, 2014.*
Real et al. Appl Microbiol Biotechnol 2011;91:1581-91.*
Zufferey et al. J Virol 1999;73:2886-92.*
Wikipedia, WHP, last revision Mar. 2018.*
Beerli, et al., "Engineering Polydactyl Zinc-Finger Transcription Factors," *Nature Biotechnology* 20:135-141(2002).
Boch, et al., "Breaking the Code of DNA Binding Specificity of Tal-Type III Effectors," *Science* 326:1509-1512 (2009).
Bonas, et al., "Genetic and Structural Characterization of the Avirulence Gene AVRBS3 From *Xanthomonas campestris* Pv. Vesicatoria," *Mol. Gen. Genet.* 218:127-136 (1989).
Breckpot, et al., "Lentivirally Transduced Dendritic Cells as a Tool for Cancer Immunotherapy," *J. Gene Med.* 5(8):654-667 (2003).

(Continued)

Primary Examiner — Qian Janice Li
(74) Attorney, Agent, or Firm — Pasternak Patent Law; Susan Abrahamson

(57) ABSTRACT

Methods and compositions for increasing transgene expression and/or activity, including for increasing nuclease-mediated genomic modifications.

11 Claims, 13 Drawing Sheets

Specification includes a Sequence Listing.

(56) References Cited

U.S. PATENT DOCUMENTS

| | | | |
|---|---|---|---|
| 8,703,489 B2 | 4/2014 | Wang | |
| 8,772,008 B2* | 7/2014 | Doyon | C12N 5/00 435/196 |
| 8,823,618 B2 | 9/2014 | Lee et al. | |
| 8,945,868 B2 | 2/2015 | Collingwood et al. | |
| 8,956,828 B2 | 2/2015 | Bonini et al. | |
| 9,005,973 B2 | 4/2015 | Cost et al. | |
| 9,045,763 B2 | 6/2015 | DeKelver et al. | |
| 9,150,847 B2 | 10/2015 | Rebar | |
| 9,200,266 B2 | 12/2015 | Wang | |
| 9,234,213 B2* | 1/2016 | Wu | C12N 15/907 |
| 9,255,250 B2 | 2/2016 | Gregory et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Umov et al. | |
| 2005/0208489 A1 | 9/2005 | Carroll et al. | |
| 2006/0063231 A1 | 3/2006 | Li et al. | |
| 2007/0134796 A1 | 6/2007 | Holmes et al. | |
| 2008/0159996 A1 | 7/2008 | Ando et al. | |
| 2008/0299580 A1 | 12/2008 | DeKelver et al. | |
| 2009/0068164 A1 | 3/2009 | Segal et al. | |
| 2010/0047805 A1 | 2/2010 | Wang | |
| 2010/0218264 A1 | 8/2010 | Cui et al. | |
| 2011/0082093 A1 | 4/2011 | Gregory et al. | |
| 2011/0207221 A1 | 8/2011 | Cost et al. | |
| 2011/0265198 A1 | 10/2011 | Gregory et al. | |
| 2011/0281361 A1 | 11/2011 | DeKelver et al. | |
| 2012/0017290 A1 | 1/2012 | Cui et al. | |
| 2012/0128635 A1 | 5/2012 | Gregory et al. | |
| 2012/0213241 A1 | 8/2012 | Lell et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |
| 2013/0177983 A1 | 7/2013 | Rebar | |
| 2013/0196373 A1 | 8/2013 | Gregory et al. | |
| 2013/0253040 A1 | 9/2013 | Miller | |
| 2013/0326645 A1 | 12/2013 | Cost et al. | |
| 2014/0017212 A1 | 1/2014 | Rebar | |
| 2014/0017214 A1 | 1/2014 | Cost | |
| 2014/0093913 A1 | 4/2014 | Cost et al. | |
| 2014/0112896 A1 | 4/2014 | Rebar | |
| 2014/0357530 A1* | 12/2014 | Zhang | C12N 15/63 506/16 |
| 2015/0056705 A1 | 2/2015 | Conway et al. | |
| 2015/0110762 A1 | 4/2015 | Holmes et al. | |
| 2016/0030477 A1 | 2/2016 | Conway et al. | |
| 2016/0060656 A1 | 3/2016 | Rebar | |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 10/079430 A1 | 7/2010 |

OTHER PUBLICATIONS

Brun, et al., "Optimization of Transgene Expression at the Post-transcriptional Level in Neural Cells: Implications for Gene Therapy," *Molecular Therapy* 7:782 (2003).

Choi, et al., "Optimization of AAV Expression Cassettes to Improve Packaging Capacity and Transgene Expression in Neurons," *Mol. Brain* 7:17 (2014).

Choo, et al., "Advances in Zinc Finger Engineering," *Curr. Opin. Struct. Biol.* 10:411-416 (2000).

Cong, et al., "Multiplex Genome Engineering Using CRISPR/CAS Systems," Sciencexpress/10.1126/science.1231143 (2013).

Cotungo, et al., "Impact of Age at Administration, Lysosomal Storage, and Transgene Regulatory Elements on AAV2/8-Mediated Rat Liver Transduction," *PLOS One* 10.1371/journal.pone.0033286 (2012).

Donello, "The Hepatitis B Virus Posttranscriptional Regulatory Element Is Composed of Two Subelements," *J. Vir.* 70:4345-4351 (1996).

Donello, "Woodchuck Hepatitis Virus Contains a Tripartite Post-transcriptional Regulatory Element," *J. Vir.* 72:5085-5092 (1998).

Dronadula, et al.,"Construction of a Novel Expression Cassette for Increasing Transgene Expression in Vivo in Endothelial Cells of Large Blood Vessels," *Gene Therapy* 18:501-508 (2010).

Esvelt, et al., "Orthogonal CAS9 Proteins for RNA-Guided Gene Regulation and Editing," *Nat. Meth.* 10(11):1116 (2013).

Fagerlund, et al., "The CPF1 CRISPR-CAS Protein Expands Genome-Editing Tools," *Genom. Bio.* 16:251 (2015).

Fonfara, et al., "Phylogeny of CAS9 Determines Functional Exchange-ability of Dual-RNA and CAS9 Among Orthologous Type II CRISPR-CAS Systems," *Nucl. Acid Research* 42(4):2377-2590 (2013).

Fu, et al., "Improving CRISPR-CAS Nuclease Specificity Using Truncated Guide RNAs," Nature Biotech. 32(3):279 (2014).

Gulinger, et al., "Fusion of Catalytically Inactive CAS9 to Foki Nuclease Improves the Specificity of Genome Modification," *Nature Biotech.* 32(6):577-582 (2014).

Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).

Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).

Higashimoto, et al., "The Woodchuck Hepatitis Virus Post-Transcriptional Regulatory Element Reduces Readthrough Transcription From Retroviral Vectors," *Gene Therapy* 14:1298-1304 (2007).

Hlavaty, et al., "Effect of Posttranscriptional Regulatory Elements on Transgene Expression and Virus Production in the Context of Retrovirus Vectors," *Virology* 10.1016/j.virol.2005.06.037 (2005).

Hsu, et al., "DNA Targeting Specificity of RNA-Guided CAS9 Nucleases," *Nature Biotechnology* 31:827-832 (2013) doi:10.1038/nbt.2647.

Huang, "Hepatitis B Virus RNA Element That Facilitates Accumulating of Surface Gene Transcripts in the Cytoplasm," *J. Virol.* 68(5):3193-3199 (1994).

Huang, "Role of the Hepatitis B Virus Posttranscriptional Regulatory Element in Export of Intronless Transcripts," *Mol. Cell. Biol.* 15:3864-3869 (1995).

Hwang et al., "Efficient in Vivo Genome Editing Using RNA-Guided Nucleases," *Nature Biotechnology* 31(3):227 (2013).

Isalan, et al., "A Rapid, Generally Applicable Method to Engineer Zinc Fingers Illustrated by Targeting the HIV-1 Promoter," *Nat. Biotechnology* 19:656-660 (2001).

Jansen, et al., "Identification of Genes That Are Associated With DNA Repeats in Prokaryotes," *Molecular Microbiology* 43(6):1565-1575 (2002).

Jinek, et al., "A Programmable Duel-RNA-Guided DNA Endonuclease in Adaptive Bacterial Immunity," *Science* 337:816-821 (2012).

Kay, et al., "A Bacterial Effector Acts as a Plant Transcription Factor and Induces a Cell Size Regulator," *Science* 318:648-651 (2007).

Kim, et al., "Hybrid Restriction Enzymes: Zinc Finger Fusions to FOK I Cleavage Domain," *PNAS USA* 93(3):1156-1160 (1996).

Klein, et al., "WPRE-Mediated Enhancement of Gene Extression is Promoter and Cell Line Specific," *Gene* 372:153-161 (2006).

Kraunus, et al., "Self-Inactivating Retroviral Vectors With Improved RNA Processing," *Gene Therapy* 11:1568-1578 (2004).

(56) References Cited

OTHER PUBLICATIONS

Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Mangeot, et al., "High Levels of Transduction of Human Dendritic Cells With Optimized SIV Vectors," *Molecular Therapy* 5:283-290 (2002).
Mautino, et al., "Enhanced Inhibition of Human Immunodeficiency Virus Type I Replication by Novel Lentiviral Vectors Expressing Human Immunodeficiency Virus Type I Envelope Antisense RNA," *Hum. Gene Therapy* 10:13(9): 1027-1037 (2002).
McCaffery, et al., "CRISPR-CAS9 D10A Nickase Target-Specific Flourescent Labeling of Double Strand DNA for Whole Genome Mapping and Structural Variation Analysis," *Nucleic Acids Res.* 44(2):e11 (2016).
Moscou, et al., "A Simple Cipher Governs DNA Recognition by TAL Effectors," *Science* 326:1501 (2009).
Perez, et al., "Establishment HIV-1 Resistance in CD4+ T Cells by Genome Editing Using Zinc-Finger Nucleases," *Nature Biotechnology* 26(7):808-816 (2008).
Perez-Pinera, et al, "RNA-Guided Gene Activation by CRISPR-CAS9-Based Transcription Factors," *Nature Methods* 10:973-976 (2013).
Piatck, et al., "RNA-Guided Transcriptional Regulation in Planta Via Synthetic DCAS9-Based Transcription Factors," *Plant Biotechnology J.* 13(4):578-89 (2015) doi:10.1111/pbi.12284; Epub 2014.
Ramezami, et al., "Lentiviral Vectors for Enhanced Gene Expression in Human Hematopoietic Cells," *Molecular Therapy* 2(5):458-469 (2000).
Sander, et al., "CRISPR-CAS Systems for Genome Editing, Regulation and Targeting," *Nature Biotech.* 32(4):347 (2015).
Schambach, et al., "Woodchuck Hepatitis Virus Post-Transcriptional Regulatory Element Deleted From X Proteln and Promoter Sequences Enhances Retroviral Vector Titer and Expression," *Gene Therapy* 13:641-645 (2006).
Schambach, et al., "Context Dependence of Different Modules for Posttranscriptional Enhancement of Gene Expression From Retroviral Vectors," *Molecular Therapy* 2:435-445 (2000).
Schomack, et al., "Gene-For-Gene-Mediated Recognition of Nuclear-Targeted AVRBS3-Like Bacterial Effector Proteins," *J. Plant Physiol.* 163(3):256-272 (2006).
Segal, el al., "Custom DNA-Binding Proteins Come of Age: Polydactyl Zinc-Finger Proteins," *Curr. Opin. Biotechnol.* 12:632-637 (2001).
Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.
Swarts, et al., "DNA-Guided DNA Interference by a Prokaryotic Argonaute" *Nature* 507(7491):258-261 (2014).
Unzu, et al., "Sustained Enzymatic Correction by RAAV-Mediated Liver Gene Therapy Protects Against Induced Motor Neuropathy in Acute Porphyria Mice," *Molecular Therapy* 19:243-250 (2010).
Umov, et al., "Highly Efficient Endoenous Human Gene Correction Using Designed ZINV-Finger Nucleases," *Nature* 435(7042):646-651 (2005).
Werner, et al., "B-Cell-Specific Transgene Expression Using a Self-Inactivating Retroviral Vector With Human CD19 Promoter and Viral Post-Transcriptional Regulatory Element," *Gene Therapy* 11(12):992-1000 (2004).
Wu, et al., "Genome-Wide Bending of the CRISPR Endonuclease CAS9 in Mammalian Cells," *Nature Biotech.* 32:670-676 (2014) doi:10.1038/nbt2889.
Yu, et al., "An Engineered VEGF-Activating Zinc Finger Protein Transcription Factor Improves Blood Flow and Limb Salvage in Advanced-Age Mice," *FASEB J.* 20:479-481 (2006).
Zanta-Boussif, et al., "Validation of a Mutated Pre Sequence Allowing High and Sustained Transgene Extression While Abrogating WHV-X Protein Synthesis: Application to the Gene Therapy of WAS," *Gene Therapy* 16:605-619 (2009).
Zhao, et al., "Recombinase-Mediated Reprogramming and Dystrophin Gene Addition in MDX Mouse Induced Pluripotent Stem Cells," *PLOS One* (2014) 10.1371/journal.pone.0096279.
Zufferey, et al., "Woodchuck Hepatitis Virus Posttranscriptional Regulatory Element Enhances Expression of Transgenes Delivered by Retroviral Vectors," *J. Virol.* 73:2886-2892 (1999).

* cited by examiner

AAVS1

IL2Rγ

CCR5

METHODS AND COMPOSITIONS FOR INCREASING TRANSGENE ACTIVITY

CROSS-REFERENCE TO RELATED APPLICATIONS

The present application claims the benefit of U.S. Provisional Application No. 62/158,277 filed May 7, 2015, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 31, 2016, is named 83250134SL.txt and is 2,703 bytes in size.

TECHNICAL FIELD

The present disclosure is in the field of genome engineering, particularly increasing transgene expression and/or activity.

BACKGROUND

Modulation of gene expression holds enormous potential for a new era in human medicine. These methodologies will allow treatment for conditions that heretofore have not been addressable by standard medical practice.

Recombinant transcription factors comprising the DNA binding domains from zinc finger proteins ("ZFPs"), TAL-effector domains ("TALEs") and CRISPR/Cas transcription factor systems have the ability to regulate gene expression of endogenous genes (see, e.g., U.S. Pat. Nos. 8,586,526; 6,534,261; 6,599,692; 6,503,717; 6,689,558; 7,067,317; 7,262,054; Perez-Pinera et al. (2013) *Nature Methods* 10:973-976; Platek et al. (2014) *Plant Biotechnology J.* doi: 10.1111/pbi.12284). Clinical trials using these engineered transcription factors containing zinc finger proteins have shown that these novel transcription factors are capable of treating various conditions. (see, e.g., Yu et al. (2006) *FASEB J.* 20:479-481).

In addition, artificial nucleases comprising the DNA binding domains from zinc finger proteins ("ZFPs"), TAL-effector domains ("TALEs"), Ttago and CRISPR/Cas nuclease systems (including Cas and/or Cfp1) have the ability to modify gene expression of endogenous genes via nuclease-mediated modification of the gene, including either homology directed repair (HDR), following non-homologous end joining (NHEJ) and/or by end capture during non-homologous end joining (NHEJ) driven processes. See, for example, U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373; 20150056705, the disclosures of which are incorporated by reference in their entireties for all purposes. Thus, these methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Introduction of a double strand break in the absence of an externally supplied repair template (e.g. "donor" or "transgene") is commonly used for the inactivation of the targeted gene via mutations (insertions and/or deletions known as "indels") introduced by the cellular NHEJ pathway.

The efficiency of transcription factor/nuclease activity can be influenced by a variety of factors such as accessibility of the target and the quality of the binding interaction between the TF or nuclease and its target nucleic acid. U.S. Pat. No. 8,772,008 describes the use of cold-shock conditions to increase nuclease activity.

However, there remains a need for additional compositions and methods for increasing activity of transgenes (e.g., nuclease, donor transgene or transcription factor) to allow for more efficient use of these powerful tools.

SUMMARY

Figure 1:
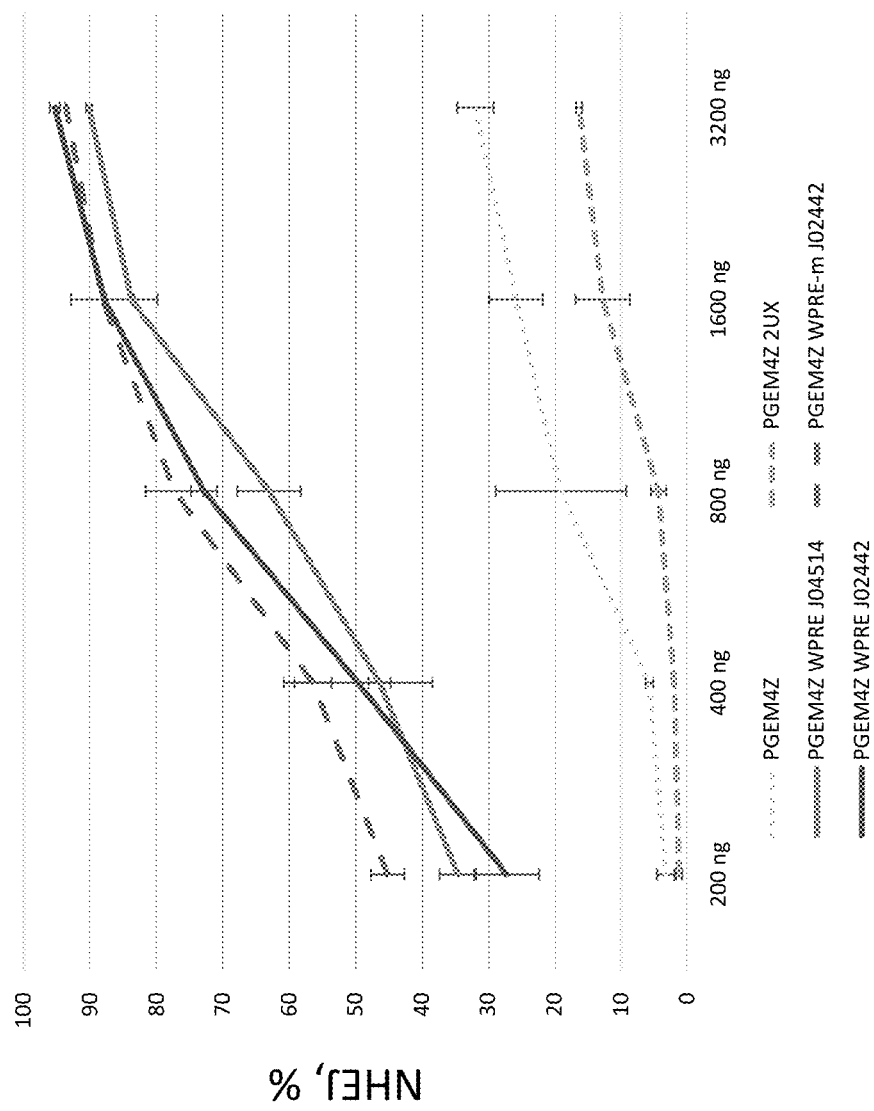
FIG. 1 depicts an assay of ZFN activity demonstrating that inclusion of a woodchuck hepatitis virus posttranslational regulatory element (WPRE; WPRE J04514 and WPRE J02442) or WPRE-mutant (WPRE-m J02442) in the 3' UTR of the mRNA encoding mouse albumin-specific ZFNs enhances nuclease-mediated NHEJ in Hepa1-6 cells. Cells transfected with messenger RNAs (mRNAs) encoding the nucleases and a WPRE sequence show enhanced nuclease cleavage activity as measured by detectable NHEJ. WPRE J04514, solid grey line; WPRE J02442, solid black line; WPRE-m J02442, long dashed line; pGEM4Z, mRNA with no UTR additions, dotted light grey line; pGEM4Z 2UX, mRNA with a dimer of the *X. laevis* beta globin 3' UTR, grey short dashed line. Error bars indicate the standard deviations of biological triplicates.

Disclosed herein are methods and compositions for increasing transgene activity. In particular, provided herein are cis-acting factors in a DNA construct and/or in an mRNA transcript that increase effective expression of transgenes encoding nucleases or transcription factors, thereby enhancing nuclease-mediated gene modification or transcription factor-mediated gene expression. In some embodiments, the cis-acting factor is in a DNA construct comprising a transgene for targeted integration into a genome.

Thus, in one aspect, a polynucleotide (e.g., expression vector, plasmid, donor, viral vector, mRNA, etc.) encoding an artificial nuclease, transgene for targeted insertion or artificial transcription factor operably linked to one or more WPRE sequences. In certain embodiments, the polynucleotide comprises a plasmid and/or mRNA.

In another aspect, the invention provides a host cell comprising at least one transgene (e.g., nuclease, transgene donor for targeted integration and/or transcription factor) expression plasmid wherein the host cell further comprises one or more WPRE sequences. In certain embodiments, the transgene is(are) and/or WPRE delivered to the cell in plasmid form. In other embodiments, transgene(s) is(are) and/or WPRE delivered to the cell in mRNA form. In other embodiments, the host cell further comprises a donor nucleic acid, wherein the donor nucleic acid is integrated into the genome of the host cell via nuclease-mediated integration. In some embodiments, the donor nucleic acid comprises a WPRE sequence. In certain embodiments, the cell is a eukaryotic cell (e.g., a mammalian yeast, insect or plant cell).

In another aspect, provided herein is a method of increasing expression of a sequence encoding one or more transgenes (e.g., nuclease(s), transgene donor for targeted integration or transcription factor(s)) within a cell, the method comprising introducing one or more WPRE sequences into the cell with polynucleotides encoding the transgene(s). In certain embodiments, the WPRE sequence is operably linked to the transgene-encoding sequences, for example in an expression vector (e.g., plasmid, viral vector) or in mRNA form. In certain embodiments, the transgene expresses one or more nucleases and the expression of the nuclease is increased at least 1.5 fold as compared to cells expressing a nuclease whose transgene sequence does not include the WPRE sequence.

In one aspect, described herein is a method for increasing activity of one or more exogenous sequences (transgenes) in a cell (e.g., in mammalian, yeast, insect or plant cells) by introducing one or more WPRE sequences into the cell with polynucleotides encoding the exogenous sequences (e.g., transcription factors, donor transgenes for targeted integration and/or nucleases). In certain embodiments, the WPRE sequence is operably linked to the transgene-encoding sequences, for example in an expression vector (e.g., plasmid, viral vector) or in mRNA form. In any of the methods described herein, the activity of the transgene (e.g., nuclease(s)) and/or transcription factor(s) may be increased at least 1.5 fold, at least 2 fold, at least 3 fold or at least 5 fold as compared to the activity of the transgene in cells where the transgene does not comprise the WRPE sequence.

For any of the methods involving nucleases, the methods may further comprise introducing an exogenous sequence into the host cell such that the nuclease mediates targeted integration of the exogenous sequence into the genome. In certain embodiments, the exogenous sequence is introduced at the same time as the nuclease(s). In some aspects, the exogenous sequence may comprise a therapeutic gene. In certain embodiments, the methods further comprising isolating the cells expressing the reporter gene. In particular for CRISPR/Cas nuclease systems, the Cas encoding sequence may comprise a WPRE, and/or the sgRNA used by the system may comprise a WPRE.

In any of the methods described herein, the genomic modification may comprise a gene disruption and/or a gene addition. Furthermore, any of the methods described herein may further comprise the step of cold-shocking the cells to further increase transgene expression and/or activity.

Also provided is a method of enhancing expression of an exogenous sequence (transgene) within a cell, the method comprising introducing an mRNA encoding the exogenous sequence into the cell, wherein the transgene mRNA is operably linked to one or more WPRE sequences.

In any of the compositions and methods described herein, the nuclease or transcription factor may comprise one or more zinc finger proteins (ZFP-TFs or ZFNs), one or more TAL-effector domain nucleases (TALE-TFs or TALENs), and/or one or more components of a TtAgo or CRISPR/Cas transcription factor or nuclease system (e.g. the Cas protein and/or the sgRNA). Furthermore, in any of the compositions or methods described herein, the WPRE sequence comprises a wild-type sequence, truncation and/or mutant (as compared to wild-type) sequence. In addition, the compositions and methods described herein may be made or practiced in vivo or ex vivo, including, but not limited to, mammalian cells such as K562 cells, Hepa1-6 cells, CD4+ T cells, CD8+ T cells, CD34+ hematopoietic stem cells (HPSCs), and in vivo (e.g., hepatocytes); yeast cells such as *S. cerevisiae* or *S. pichia*; insect cells such as SF-9 cells, and plant cells derived from maize, wheat or canola.

In another aspect, the invention provides kits that are useful for increasing expression and/or activity of one or more transgenes (e.g., ZFP-TFs, TALE-TFs, ZFNs, TAL-effector domain nuclease fusion proteins, engineered homing endonucleases, Ttago, CRISPR/Cas transcription factor, sgRNA or nuclease systems). The kits typically include one or more nucleases that bind to a target site, optional cells containing the target site(s) of the transcription factor or nuclease and instructions for introducing the nucleases into the cells and providing one or more WPRE sequences to the cells to increase transcription factor or nuclease expression and/or activity. Other kits contemplated by the invention may include a known nuclease capable of cleaving within a known target locus within a genome, and may additionally comprise a donor nucleic acid encoding a reporter gene or therapeutic gene. Such kits are useful for optimization of conditions for donor integration. In such kits, the donor may be operatively linked to a polyadenylation signal and/or a regulatory element (e.g. a promoter).

These and other aspects will be readily apparent to the skilled artisan in light of disclosure as a whole.

DETAILED DESCRIPTION

Disclosed herein are methods and compositions for increasing transgene activity, including transgenes encoding artificial transcription factors, donor transgenes for targeted integration or nucleases. In particular, using a Woodchuck Posttranslational regulator element (WPRE) polynucleotide or derivative or truncation thereof in combination with the transgenes (including polynucleotides encoding the transgene(s)) surprisingly and unexpectedly results in increased transgene expression and activity.

WPRE has been used to stabilize the expression of a gene in viral vectors (e.g., lentiviral, AAV vectors, etc.) in cases where the viral vector lacks a polyA signal. In particular, WPRE has been used in place of the polyA signal in vectors where the polyA interferes with the viral vector (e.g., interferes with viral vector replication) as a means for increasing importation of the viral vector into the nucleus in the absence of the polyA signal. Surprisingly and unexpectedly, the present inventors have found that WPRE increases transgene expression, including expression from vectors comprising a gene expression cassette for in vitro expression of mRNA (which include a polyA tail when transcribed), as well as premade transgene mRNAs with polyA tails delivered to the cytoplasm. Furthermore, the present disclosure surprisingly demonstrates that inclusion of WPRE with mRNA transgenes that also include a polyA signal provides increased expression as compared to mRNA with the polyA tail alone.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; 6,746,838; 7,241,573; 6,866,997; 7,241,574 and 6,534,261; see also and WO03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; 6,242, 568; 6,733,970; 7,297,491; WO 98/53057; WO 02/099084.

"TtAgo" is a prokaryotic Argonaute protein thought to be involved in gene silencing. TtAgo is derived from the bacteria *Thermus thermophilus*. See, e.g., Swarts et al. (2014) *Nature* 507(7491):258-61; G. Sheng et al., (2013) *Proc. Natl. Acad. Sci. U.S.A.* 111, 652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Recombination" refers to a process of exchange of genetic information between two polynucleotides. For the purposes of this disclosure, "homologous recombination" (HR) refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell. In addition, a CRISPR/Cas system may be similarly employed to induce additional double strand breaks.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cells and cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598 and 8,823,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins, for example, a fusion between a DNA-binding domain (e.g., ZFP, TALE and/or meganuclease DNA-binding domains) and a functional domain (e.g., endonuclease, meganuclease, ZFP-transcription factor, (ZFP-TF), TALE-transcription factor (TALE-TF), CRIPSR/Cas transcription factor (CRISPR/Cas-TF) etc.) and fusion nucleic acids (for example, a nucleic acid encoding a fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (ZFP, TALE) is fused to a cleavage domain (e.g., endonuclease domain such as FokI, meganuclease domain, etc.), the DNA-binding domain and the cleavage domain are in operative linkage if, in the fusion polypeptide, the DNA-binding domain portion is able to bind its target site and/or its binding site, while the cleavage (nuclease) domain is able to cleave DNA in the vicinity of the target site. The nuclease domain may also exhibit DNA-binding capability (e.g., a nuclease fused to a ZFP or TALE domain that also can bind to DNA). Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to up regulate gene expression or the repression domain is able to down regulate gene expression. In addition, a fusion polypeptide in which a Cas DNA-binding domain is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, rabbits and other animals.

WPRE Polynucleotides

Since its identification from the Woodchuck hepatitis B virus (see, Donello (1998) *J. Vir.* 72:5085-5092), the WPRE has been the subject of intense investigation regarding its role in nuclear transport (e.g., export of mRNA and/or important of viral vectors lacking a polyA tail), in particular un-spliced mRNA (such as WHV mRNA). Donello's work (ibid) demonstrated that WPRE is approximately 600 base pair in length and comprises three independent sub-elements termed WPREα, WPREβ and WPREΥ in the order Υ-α-β. Later work done by Choi et al ((2014) *Mol Brain* 7:17) showed that a truncated WPRE comprising only minimal gamma and alpha elements (termed WPRE3) was effective in increasing transgene expression. However, the effect of the WPRE is highly variable between different cells and/or expression vectors: sometimes its inclusion has no effect on transgene or mRNA levels; sometimes its inclusion improves transgene expression; and, in some instances, sometimes its inclusion actually inhibits transgene expression. See, e.g., Zufferey et al. (1999) *J. Vir.* 73:2886-2892; Ramezami et al. (2000) *Molecular Therapy* 2(5):458-69; Schambach et al. (2000) *Molecular Therapy* 2:43 5-445; Mautino et al. (2002) *Hum Gene Ther.* 2002 Jun. 10; 13(9):1027-37; Mangeot et al. (2002) *Molecular Therapy* 5:283-290; Brun et al. (2003) *Molecular Therapy* 7:782; Breckpot et al. (2003) *J Gene Med.* 5(8):654-67; Kraunus et al. (2004) *Gene Therapy* (2004) 11:1568-78; Hlavaty et al. (2005) *Virology* 10.1016/j.virol.2005.06.037; Schambach et al. (2006) *Gene Therapy* 13:641-45; Klein et al. (2006) *Gene* 372: 153-161; Higashimoto et al. (2007) *Gene Therapy* 14:1298-1304 doi:10.1038/sj.gt.3302979; Zanta-Boussif et al. (2009) *Gene Therapy* 16:605-619; Unzu et al. (2010) *Molecular Therapy* 19:243-50; Dronadula et al. (2010) *Gene Therapy* 18:501-508; Cotungo et al. (2012) *PLoS One* 10.1371/journal.pone.0033286; Werner et al (2004) *Gene Therapy* 11:992-1000; Zhao et al. (2014) *PLoS One* 10.1371/journal.pone.0096279.

Thus, in light of the state of the art showing highly variable effects of WPRE on transgene expression, it is entirely surprising and unexpected that inclusion of this element would increase expression and/or activity of transgenes, including nuclease(s) and/or transcription factors introduced as transgenes. Further, it is particularly surprising and unexpected that the WPRE, a sequence element that promotes nuclear export of mRNA and has therefore is used only in the context of plasmid and viral vectors, would have a beneficial effect on transgene expression derived from mRNA transfection as transfected mRNA does not require nuclear export: it enters the cytoplasm and can be translated directly by the ribosome. Similarly, it is surprising and unexpected that WRPE, which has been used in place of a polyA tail in viral vectors, would increase transgene expression from mRNA that includes a polyA signal.

Any WPRE sequence can be used in the practice of the present invention. Non-limiting examples of suitable sequences are disclosed above and in U.S. Pat. Nos. 6,136, 597; 6,284,469; 6,312,912; and 6,287,814. In certain embodiments, the WPRE sequence comprises a mutation as compared to wild-type. See, e.g., U.S. Pat. No. 7,419,829 and Zanta-Boussif et al. (2009) *Gene Therapy* 16:605-619 or a truncation (Choi et al, ibid). One or more of the same or different WPRE sequences may also be used.

In certain embodiments, the WPRE sequence comprises a sequence from the Woodchuck hepatitis virus (WHV) J04514 genome as follows:

```
                                           (SEQ ID NO: 1)
aatcaacctctggattacaaaatttgtgaaagattgactggtattcttaa ctatgttgctcctttacgctatgtggatacgctgctttaatgcctttgt atcatgctattgcttcccgtatggctttcattttctcctccttgtataaa tcctggttgctgtctctttatgaggagttgtggcccgttgtcaggcaacg tggcgtggtgtgcactgtgtttgctgacgcaacccccactggttggggca ttgccaccacctgtcagctcctttccgggactttcgctttccccctccct attgccacggcggaactcatcgccgcctgccttgcccgctgctggacagg ggctcggctgttgggcactgacaattccgtggtgttgtcggggaagctga cgtcctttccatggctgctcgcctgtgttgccacctggattctgcgcggg acgtccttctgctacgtccctccggccctcaatccagcggaccttccttc ccgcggcctgctgccggctctgcggcctcttccgcgtcttcgccttcgcc ctcagacgagtcggatctccctttgggccgcctccccgcctg
```

In other embodiments, the WPRE sequence comprises a sequence from the Woodchuck hepatitis virus (WHV) J02442 genome as follows:

```
                                           (SEQ ID NO: 2)
aatcaacctctggattacaaaatttgtgaaagattgactgatattcttaa ctatgttgctcctttacgctgtgtggatatgctgctttaatgcctctgt atcatgctattgcttcccgtacggctttcgttttctcctccttgtataaa
```

-continued
```
tcctggttgctgtctctttatgaggagttgtggcccgttgtccgtcaacg tggcgtggtgtgctctgtgtttgctgacgcaaccccactggctggggca ttgccaccacctgtcaactcctttctgggactttcgctttcccctcccg atcgccacggcagaactcatcgccgcctgccttgcccgctgctggacagg ggctaggttgctgggcactgataattccgtggtgttgtcggggaagctga cgtcctttccatggctgctcgcctgtgttgccaactggatcctgcgcggg acgtccttctgctacgtcccttcggctctcaatccagcggacctcccttc ccgaggccttctgccggttctgcggcctctcccgcgtcttcgctttcggc ctccgacgagtcggatctccctttgggccgcctcccgcctg
```

In other embodiments, the WPRE sequence comprises a truncated sequence from the Woodchuck hepatitis virus (WHV), WPRE3 as follows:

```
                                        (SEQ ID NO: 3)
AATCAACCTCTGGATTACAAAATTTGTGAAAGATTGACTGGTATTCTTAA

CTATGTTGCTCCTTTTACGCTATGTGGATACGCTGCTTTAATGCCTTTGT

ATCATGCTATTGCTTCCCGTATGGCTTTCATTTTCTCCTCCTTGTATAAA

TCCTGGTTAGTTCTTGCCACGGCGGAACTCATCGCCGCCTGCCTTGCCCG

CTGCTGGACAGGGGCTCGGCTGTTGGGCACTGACAATTCCGTGGT
```

The WPRE sequence(s) may be introduced concurrently and/or sequentially with the transgene (i.e., the polynucleotide encoding the nuclease(s)). In certain embodiments, one or more WPRE sequence(s) are carried on the same vector as the nuclease(s) (e.g., in the same mRNA or on the same plasmid). In other embodiments, one or more WPRE sequence(s) are found on one or more different polynucleotides (e.g., vectors). In certain embodiments, the transgenes (nucleases) are introduced in plasmid form the plasmid(s) include one or more WPRE sequences operably linked to the nuclease-encoding sequences. In other embodiments, the nucleases are introduced in mRNA form operably linked to a WPRE. In still further embodiments, the nuclease(s) is(are) introduced in mRNA form and the WPRE sequence(s) is(are) introduced on plasmids.

The human hepatitis B virus (HBV) contains a post-transcriptional response element analogous to the one found in woodchuck hepatitis virus. The HBV PRE functions similarly to the WHV PRE, causing the nuclear export of unspliced mRNA (see, Donello (1998)*J. Vir.* 72:5085-5092; Donello (1996)*J. Vir.* 70:4345-4351; Huang (1994) *J. Vir.* 68; 3193-3199; Huang (1995) *Mol. Cell. Biol.* 15; 3864-3869). In certain embodiments, the WPRE sequence comprises an HBV PRE sequence.

Transgenes

The compositions and methods described herein can be used for increasing expression and/or activity of any transgene, including, but not limited to, transgenes encoding transcriptional regulators, donor transgenes for targeted integration and/or nucleases. The transgenes (e.g., in mRNA form) can encode fusion proteins, for example DNA-binding domains fused to functional domains (e.g., transcriptional activation domains, transcriptional repression domains and/or nucleases) or encode components (e.g. the Cas protein and/or sgRNA) of a transcription factor or nuclease system such as the CRISPR/Cas system.

A. DNA-Binding Domains

The methods and compositions described herein can be used to increase expression and/or activity of any transgene comprising a DNA-binding domain, including but not limited to a zinc finger DNA-binding domain, a TALE DNA binding domain, or a DNA-binding domain from a meganuclease, or a CRIPSR/Cas DNA binding complex.

In certain embodiments, the composition comprises a DNA-binding domain and/or nuclease (cleavage) domain from a meganuclease (homing endonuclease). Naturally-occurring meganucleases recognize 15-40 base-pair cleavage sites and are commonly grouped into four families: the LAGLIDADG family ("LAGLIDADG" disclosed as SEQ ID NO: 4), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the homing endonuclease (meganuclease) is engineered (non-naturally occurring). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, U.S. Pat. No. 8,021,867; Chevalier et al. (2002) *Molec. Cell* 10:895-905; Epinat et al. (2003) *Nucleic Acids Res.* 31:2952-2962; Ashworth et al. (2006) *Nature* 441:656-659; and Paques et al. (2007) *Current Gene Therapy* 7:49-66. The DNA-binding domains of the homing endonucleases and meganucleases may be altered in the context of the nuclease as a whole (i.e., such that the nuclease includes the cognate cleavage domain) or may be fused to a heterologous DNA-binding domain (e.g., zinc finger protein or TALE) or to a heterologous cleavage domain. DNA-binding domains derived from meganucleases may also exhibit DNA-binding activity.

In other embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989)*Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appland Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and *Ralstonia* (see Heuer et al (2007) *Applied and Environmental Microbiology* 73(13): 4379-4384); U.S. Pat. Nos. 8,586,526; 8,420,782 and 8,440,431.

In certain embodiments, the DNA binding domain comprises a zinc finger protein (e.g., a zinc finger protein that binds to a target site in a selected gene). Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 7,888,121; 7,972,854; 6,453,242; 6,534,261; 6,599,692; 6,503,717; 6,689,558; 7,030,215; 6,794,136; 7,067,317; 7,262,054; 7,070,934; 7,361,635; 7,253,273, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 8,586,526; 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 8,586,526; 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, DNA-binding domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In still further embodiments, the DNA binding domain comprises a single-guide RNA in combination with a CRISPR/Cas nuclease system or a CRISPR/Cas transcription factor.

B. Functional Domains

The DNA-binding domains may be operably linked to any functional domain.

In certain embodiments, the functional domain comprises a transcriptional regulatory domain, including an activation domain or a repression domain. Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999)*J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain as described herein and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Pat. Nos. 6,919,204 and 7,053,264.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

In certain embodiments, the target site bound by the DNA-binding domain is present in an accessible region of cellular chromatin. Accessible regions can be determined as described, for example, in U.S. Pat. No. 6,511,808. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

In other embodiments, the functional (regulatory) domain comprises a nuclease (cleavage) domain. Any suitable cleavage domain can be operatively linked to any DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. See, for example, U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20100218264; 20120017290; 20110265198; 20130137104; 20130122591; 20130177983 and 20130177960. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains), or a generic nuclease guided by a specific guide RNA (e.g. a CRPISR/Cas).

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

In some embodiments, a Cas protein may be linked to a heterologous nuclease domain. In some aspects, the Cas protein is a Cas9 or Cfp1 protein devoid of nuclease activity linked to a FokI nuclease domain such that double strand cleavage is dependent on dimerization of the FokI nuclease domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al.

(1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,888,121; 8,409,861; 7,914,796; and 8,034,598, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Pat. Nos. 7,914,796 and 8,034,598, the disclosures of which are incorporated by reference in their entireties, the disclosures of which are incorporated by reference in their entireties for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Pat. No. 8,623,618, incorporated by reference herein).

Engineered cleavage half-domains described herein can be prepared using any suitable method, for example, by site-directed mutagenesis of wild-type cleavage half-domains (Fok I) as described in U.S. Pat. Nos. 7,888,121; 7,914,796 and 8,034,598.

Alternatively, nucleases may be assembled in vivo at the nucleic acid target site using so-called "split-enzyme" technology (see, e.g., U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

The nuclease domain may also be derived from a homing endonuclease (meganuclease). Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Thus, the nuclease as described herein can comprise any DNA-binding domain and any nuclease.

In certain embodiments, the nuclease comprises a zinc finger DNA-binding domain and a restriction endonuclease nuclease domain, also referred to as a zinc finger nuclease (ZFN).

In other embodiments, the nuclease comprises an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et al (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Nucleases can be screened for activity prior to use, for example in a yeast-based chromosomal system as described in U.S. Pat. No. 8,563,314. Nuclease expression constructs can be readily designed using methods known in the art. See, e.g., U.S. Pat. Nos. 7,888,121 and 8,409,861; 20030232410; 20050208489; 20050026157; 20060063231; and 20070134796. Expression of the nuclease may be under the control of a constitutive promoter or an inducible promoter, for example the galactokinase promoter which is activated (de-repressed) in the presence of raffinose and/or galactose and repressed in presence of glucose.

In certain embodiments, the nuclease or transcription factor comprises a CRISPR/Cas system. See, e.g., U.S. Pat. No. 8,697,359. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA: tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

Type II CRISPR systems have been found in many different bacteria. BLAST searches on publically available genomes by Fonfara et al ((2013) *Nucl Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas" refers to an RNA guided DNA nuclease comprising a DNA binding domain and two nuclease domains, where the gene encoding the Cas may be derived from any suitable bacteria.

The Cas protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas nuclease can be engineered such that only one of the nuclease domains is functional, creating a Cas nickase (see Jinek et al, ibid). Nickases can be generated by specific mutation of amino acids in the catalytic domain of the enzyme, or by truncation of part or all of the domain such that it is no longer functional. Since Cas comprises two nuclease domains, this approach may be taken on either domain. A double strand break can be achieved in the target DNA by the use of two such Cas nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek et al (2012) *Science* 337:816 and Cong et al (2013) Sciencexpress/10.1126/science.1231143). In *S. pyogenes*, the engineered tracrRNA:crRNA fusion, or the sgRNA, guides the functional domain (e.g., Cas or other functional domain) to modify the target DNA, for example when a double strand RNA:DNA heterodimer forms between the Cas associated RNAs and the target DNA in the case of a nuclease. This system comprising the Cas9 protein and an engineered sgRNA containing a PAM sequence has been used for RNA guided genome editing (see Ramalingam ibid) and has been useful for zebrafish embryo genomic editing in vivo (see Hwang et al (2013) *Nature Biotechnology* 31 (3):227) with editing efficiencies similar to ZFNs and TALENs.

Chimeric or sgRNAs can be engineered to comprise a sequence complementary to any desired target. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In certain embodiments, the RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et al (2013) *Nature Biotech* doi:10.1038/nbt.2647). Tails may be of +67 to +85 nucleotides, or any number therebetween with a preferred length of +85 nucleotides. Truncated sgRNAs may also be used, "tru-gRNAs" (see Fu et al, (2014) *Nature Biotech* 32(3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2014, ibid) using a *S. pyogenes* Cas9. Additional PAM sequences may also include those lacking the initial G (Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below (adapted from Sander and Joung, ibid, and Esvelt et al, (2013) *Nat Meth* 10(11): 1116) are specific for these Cas9 proteins:

| Species | PAM |
| --- | --- |
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a *S. pyogenes* CRISPR/Cas system can be chosen according to the following guideline: [n17, n18, n19, or n20](G/A)G. Alternatively the PAM sequence can follow the guideline G[n17, n18, n19, n20](G/A)G. For Cas proteins derived from non-*S. pyogenes* bacteria, the same guidelines may be used where the alternate PAMs are substituted in for the *S. pyogenes* PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al (2014) *Nature Biotech* doi: 10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2014, ibid).

Thus, by performing an analysis of the number of potential off target sites in a genome for whichever CRIPSR/Cas system is being employed, using these criteria above, a suitable target sequence for the sgRNA may be identified.

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al, (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Thus, as used herein, a "CRISPR/Cas system" refers both CRISPR/Cas and/or CRISPR/Cfp1 systems, including both nuclease and/or transcription factor systems.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to specific genes are disclosed for example, in U.S. Publication No. 20150056705.

The nuclease(s) as described herein may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):e11. doi: 10.1093/nar/gkv878. Epub 2015 Oct. 19.

Thus, the nuclease comprises a DNA-binding domain (e.g., ZFP, TALE, sgRNA) in that specifically binds to a target site in any gene into which it is desired to insert a donor (transgene) in combination with a nuclease domain that cleaves DNA.

C. Additional Proteins

As noted above, the compositions and methods described herein can be used to increase expression of any transgene, e.g., a transgene introduced in mRNA form. Non-limiting examples of transgenes include proteins that are lacking, deficient and/or non-functional in the subject having a disease, including but not limited to any of the following diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trinucleotide repeat disorders, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240). See, e.g., U.S. Patent Publication Nos. 20130253040; 20120128635; 20120213241; and 20110082093.

Additional exemplary therapeutic proteins that can be expressed using the methods and compositions described herein include proteins lacking and/or deficient in immunodeficiencies, HLA-related disorders, cancers, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias. See, e.g., U.S. Pat. Nos. 8,956,828 and 8,945,868; U.S. Patent Publication Nos. 20140017214 and 2014-0093913.

In certain embodiments, transgene can comprise a marker gene (described above), allowing selection of cells that have undergone targeted integration, and a linked sequence encoding an additional functionality. Non-limiting examples of marker genes include GFP, drug selection marker(s) and the like.

Target Sites

As described in detail above, DNA-binding domains (e.g., ZFPs, TALEs, single-guide RNAs) can be engineered to bind to any sequence of choice in a locus.

In certain embodiments, the DNA-binding domains bind to a safe harbor gene. Non-limiting examples of safe harbor genes (including for targeted of exogenous molecules such as sequences encoding therapeutic proteins) include, for example, a CCR5 gene, a CXCR4 gene, an HPRT gene, a PPP1R12C (also known as AAVS1) gene, an albumin gene or a Rosa gene. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983; 20130177960; 20140017212; and 20140112896.

Donors

As noted above, the compositions and methods described herein can be used to modify one or more genes in any way, including but not limited to, inactivation and/or insertion of an exogenous sequence. With regard to insertion of an exogenous sequence (also called a "donor sequence" or "donor" or "transgene"), it will be readily apparent that the donor sequence need not be identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest. Alternatively, a donor molecule may be integrated into a cleaved target locus via non-homologous end joining (NHEJ) mechanisms. See, e.g., U.S. Patent Publication Nos. 20110207221 and 20130326645.

Described herein are methods of increasing targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805; 20110281361; and 20110207221. The donor sequence(s)

can be contained within a DNA minicircle (MC), which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 1 target site, for example, for use with a CRISPR/Cas, or 2 target sites, for example for a pair of ZFNs and/or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into a selected locus such that some or none of the endogenous sequences are expressed, for example as a fusion with the transgene. In other embodiments, the transgene is integrated into any endogenous locus, for example a safe-harbor locus. Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to any polypeptide involved in any disease or disorder, antibodies, antigens, enzymes, receptors (cell surface or nuclear), hormones, lymphokines, cytokines, reporter polypeptides, growth factors, and functional fragments of any of the above. The coding sequences may be, for example, cDNAs. Non-limiting examples of polypeptides that may be encoded by the exogenous (donor) sequences include growth factors (e.g., growth hormone, insulin-like growth factor-1, platelet-derived growth factor, epidermal growth factor, acidic and basic fibroblast growth factors, transforming growth factor-(3, etc.), to treat growth disorders or wasting syndromes; and antibodies (e.g., human or humanized), to provide passive immunization or protection of a subject against foreign antigens or pathogens (e.g., *H. Pylori*), or to provide treatment of cancer, arthritis or cardiovascular disease; cytokines, interferons (e.g., interferon (INF), INF-a2b and 2a, INF-aN1, INF-(31b, INF-gamma), interleukins (e.g., IL-1 to IL 10), tumor necrosis factor (TNF-a TNF-R), chemokines, granulocyte macrophage colony stimulating factor (GM-CSF), polypeptide hormones, antimicrobial polypeptides (e.g., antibacterial, antifungal, antiviral, and/or antiparasitic polypeptides), enzymes (e.g., adenosine deaminase), gonadotrophins, chemotactins, lipid-binding proteins, filgastim (Neupogen), hemoglobin, erythropoietin, insulinotropin, imiglucerase, sarbramostim, tissue plasminogen activator (WA), urokinase, streptokinase, phenylalanine ammonia lyase, brain-derived neurotrophic factor (BDNF), nerve growth factor (NGF), thrombopoietin (TPO), superoxide dismutase (SOD), adenosine deamidase, catalase calcitonin, endothelian, L-asparaginase pepsin, uricase trypsin, chymotrypsin elastase, carboxypeptidase lactase, sucrase intrinsic factor, calcitonin parathyroid hormone (PTH)-like, hormone, soluble CD4, and antibodies and/or antigen-binding fragments (e.g, FAbs) thereof (e.g., orthoclone OKT-3 (anti-CD3), GPllb/lla monoclonal antibody).

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor (transgene) polynucleotides and compositions comprising the proteins and/or polynucleotides described herein may be delivered in vivo or ex vivo by any suitable means.

Methods of delivering nucleases as described herein are described, for example, in U.S. Pat. Nos. 8,586,526; 6,453, 242; 6,503,717; 6,534,261; 6,599,692; 6,607,882; 6,689, 558; 6,824,978; 6,933,113; 6,979,539; 7,013,219; and 7,163, 824, the disclosures of all of which are incorporated by reference herein in their entireties.

Nucleases and/or donor constructs as described herein may also be delivered using vectors containing sequences encoding one or more of compositions described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979, 539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and/or donors in cells (e.g., mammalian cells) and target tissues. Non-viral vector delivery systems include mRNA, DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994). In certain embodiments, the transgene is delivered in mRNA form.

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1): 10-20 (1997); Dranoff et al., *Hum. Gene Ther.* 1:111-2 (1997).

Vectors suitable for introduction of polynucleotides described herein also include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 20090117617.

Recombinant adeno-associated virus vectors (rAAV) may also be used to deliver the compositions described herein. All vectors are derived from a plasmid that retains only the AAV inverted terminal repeats flanking the transgene expression cassette. Efficient gene transfer and stable transgene delivery are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, pseudotyped AAV such as AAV2/8, AAV2/5 and AAV2/6 and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and $\psi$2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, intrathecal, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

In certain embodiments, the compositions (including fusion proteins, CRISPR/Cas systems and/or modified cells) as described herein (e.g., polynucleotides and/or proteins) are delivered directly in vivo. The compositions (cells, polynucleotides and/or proteins) may be administered directly into the CNS, including but not limited to direct injection (including grafting of cells) into the brain or spinal cord. See, e.g., U.S. Pat. No. 5,529,774 regarding in vivo administration of polynucleotide vectors to the CNS and U.S. Pat. Nos. 5,082,670 and 6,451,306 regarding cell grafting. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, intrathecal, subdermal, and/or intracranial infusion). Cell-containing compositions may be administered into the nervous system directly, for example by grafting. Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668; 8,092,429, relating to a needle assembly for delivery of compositions to the brain and U.S. Patent Publication No. 20060239966 as well as U.S. Pat. Nos. 6,180,613 and 6,503,888 (AAV-mediated delivery of DNA to cells of the nervous system) and U.S. Pat. Nos. 6,998,118 and 7,101,540 (gene delivery to neuronal cells), incorporated herein by reference in their entireties.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example to provide a therapeutic protein via nuclease-mediated integration of a gene encoding a protein aberrantly expressed in a subject.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Methods of cell therapy to the NS are known. Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells, any plant cell (differentiated or undifferentiated) as well as insect cells such as *Spodoptera fugiperda* (Sf), or fungal cells such as *Saccharomyces, Pichia* and *Schizosaccharomyces.* In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR/Cas). Suitable primary cells include neuronal cells, peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow.

Stem cells that have been modified may also be used in some embodiments. For example, stem cells that have been made resistant to apoptosis may be used as therapeutic compositions where the stem cells also contain the ZFPs, TALEs, ZFNs, TALENs, CRISPR/Cas systems and/or donors of the invention. Resistance to apoptosis may come about, for example, by knocking out BAX and/or BAK using BAX- or BAK-specific nucleases (see, U.S. Pat. No. 8,597,912) in the stem cells, or those that are disrupted in a caspase, again using caspase-6 specific ZFNs for example. Alternatively, resistance to apoptosis can also be achieved by the use of caspase inhibitors like Z-VAD-FMK (carbobenzoxy-valyl-alanyl-aspartyl-[O-methyl]-fluoromethylketone).

Vectors (e.g., retroviruses, adenoviruses, liposomes, etc.) containing therapeutic ZFPs, TALEs, ZFNs, TALENs, CRISPR/Cas system and/or donor nucleic acids can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The following Examples relate to exemplary embodiments of the present disclosure in which the transgene encodes at least one zinc finger nuclease (ZFN) or at least one TAL-effector nuclease (TALEN). It will be appreciated that this is for purposes of exemplification only and that expression and/or activity of other nucleases can also be increased using the compositions and methods described herein, for instance TALENs (including Mega-TALs and/or compact TALENs), homing endonucleases (meganucleases) with engineered DNA-binding domains and/or fusions of naturally occurring of engineered homing endonucleases (meganucleases) and DNA-binding domains and heterologous cleavage domains, Ttago nuclease systems and/or a CRISPR/Cas or Cpf1 CRISPR/Cas system comprising an engineered single guide RNA. It will also be appreciated that these examples serve as exemplification for use when the transgene encodes an engineered (artificial) transcription factor (e.g. ZFP-TF, TALE-TF, CRISPR/Cas-TF) or component thereof as well as other transgenes.

EXAMPLES

Example 1: Preparation of ZFNs

ZFNs targeted to various genes used in this study were designed and incorporated into plasmids (e.g., pGEM) essentially as described in Urnov et al. (2005) *Nature* 435(7042):646-651, Perez et al (2008) *Nature Biotechnology* 26(7): 808-816, and U.S. Patent Publication 20080299580. The plasmids were linearized and mRNA produced from them.

Zinc finger nucleases tested included ZFNs targeted to albumin (see, U.S. Patent Publication No. 20130177983 and 20160060656), CCR5 (see, U.S. Pat. No. 7,951,925), AAVS1 (see, U.S. Pat. No. 8,110,379 and US Publication No. 20150110762) and ILRγ (see, U.S. Pat. No. 7,888,121 and US Publication No. 20160030477). The cleavage domains fused to the ZFPs included engineered FokI cleavage domains ("ELD" and "KKR") as described in U.S. Pat. No. 8,623,618. Control nucleic acids included only nuclease encoding sequences while the WPRE nucleic acids included WPRE sequences (J04514 wild-type, J02442 wild-type or J02442 mutant) operably linked to the nuclease-encoding sequences.

Example 2: Increased Frequency of Nuclease Driven NHEJ of Alleles in the Presence of WPRE Sequences ZFN activity was increased up to several fold when WPRE sequences were present in the 3' UTR. Briefly, the nucleic acids (mRNA) encoding the ZFNs or ZFNs with WPRE sequence fusions were introduced into 200,000 K562 cells, Hepa-1 cells, CD34+ cells, CD4+ cells, CD8+ cells, HepG2 cells, and mouse hepatocytes by the methods shown in the table below.

TABLE 1

| Transfection/delivery to various cell types ||
| --- | --- |
| Cell type | Transfection/delivery |
| K562s cells | Lonza Amaxa Nucleofector, solution SF, program FF-120 |
| Hepa1-6 cells | Lonza Amaxa Nucleofector, solution SG, program DS-150 |

TABLE 1-continued

Transfection/delivery to various cell types

| Cell type | Transfection/delivery |
| --- | --- |
| CD34+ HSPCs | BTX ECM 830, BTXpress solution, mode LV, 250 V, 4 ms pulse |
| CD4+ T cells | BTX ECM 830, BTXpress solution, mode LV, 250 V, 4 ms pulse |
| CD8+ T cells | BTX ECM 830, BTXpress solution, mode LV, 250 V, 4 ms pulse |
| HepG2 cells | Lonza Amaxa Nucleofector, solution SG, program EH-100 |
| Mouse liver cells | Lipid nanoparticles |

Cells were harvested and chromosomal DNA prepared using a Quickextract™ Kit according to manufacturer's directions (Epicentre®). The appropriate region of the target locus was PCR amplified using Accuprime™ High-fidelity DNA polymerase (Invitrogen) and primers containing 5' and 3' extensions required for in situ amplification on an Illumina Miseq DNA sequencing machine. These samples were then further amplified using primers that attach a sample-specific barcode. Barcoded samples were pooled and sequenced on an Illumina Miseq DNA sequencing machine. DNA sequence reads were inspected and nuclease activity ("NHEJ") assayed as the fraction that showed evidence for mutagenesis near the expected cleavage site.

Nuclease activity increased in the cells with plasmids including WPRE sequences. FIG. 1 shows exemplary results using mouse albumin-targeted ZFNs in Hepa-1 cells. FIGS. 4 and 6 to 8 show exemplary results using CCR5-targeted ZFNs in K562 (FIG. 4), CD34+ (FIG. 6), CD8+ (FIG. 7) and CD4+ cells (FIG. 8), respectively. Similar results were obtained with ZFNs targeted to AAVS1 and ILRγ.

Figure 3:
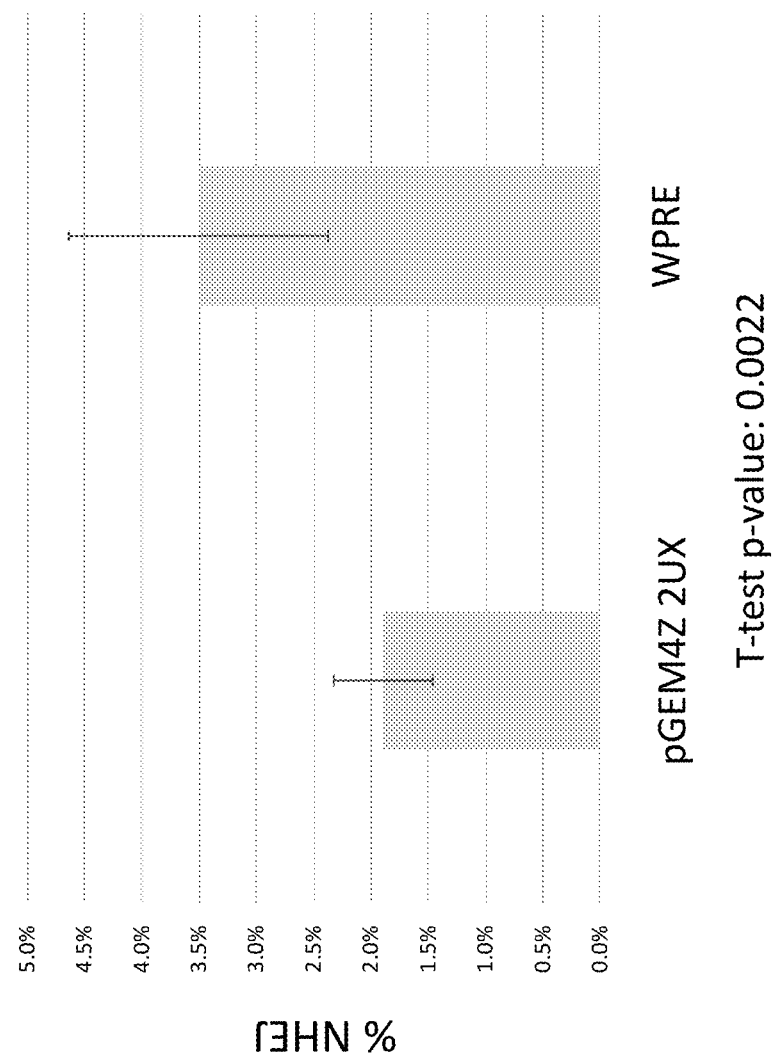
FIG. 3 is a graph depicting increased nuclease-mediated NHEJ in mouse livers following AAV mediated delivery of albumin-specific nucleases comprising the WPRE J04514 3' UTR.
Figure 4:
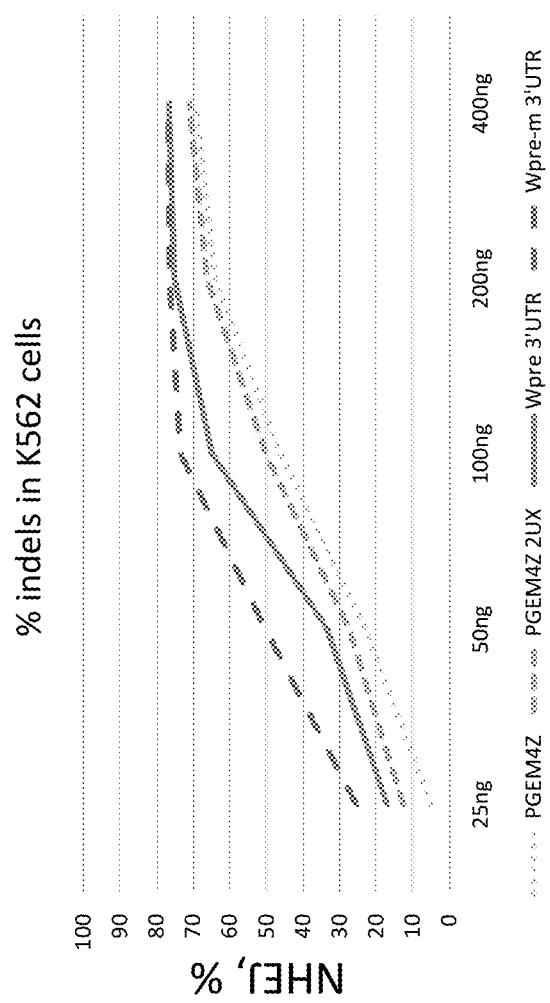
FIG. 4 depicts WPRE J04514 and WPRE-m J02442-mediated enhancement of nuclease-mediated NHEJ in K562 cells. Cells transfected with mRNAs encoding the nucleases and either WPRE sequence show enhanced nuclease associated NHEJ. WPRE J04514, solid line; WPRE-m J02442, long dashed line; pGEM4Z, dotted light grey line; pGEM4Z 2UX, grey short dashed line.

WPRE sequences also increased ZFN activity in vivo. FIG. 3 shows increased (up to 85%) of NHEJ in mouse liver following introduction of mouse albumin-targeted ZFNs operably linked to WPRE sequences as compared to ZFNs alone.

A summary of the results in a variety of cell types using a variety of ZFNs is shown in Table 2.

TABLE 2

Summary ZFN activity in the presence of a WPRE

| Target cell type | ZFN target site | Fold increase in NHEJ compared to no WPRE |
| --- | --- | --- |
| K562 | CCR5 | 1.1-2.4 |
| Hepa 1-6 | Albumin | 1.8-7 |
| in vivo mouse liver cells | Albumin | 1.85 |
| CD34+ | CCR5 | 1.8-10 |
| CD4+ | CCR5 | 1.7-4.5 |
| CD8+ | CCR5 | 2-8.5 |

Thus, inclusion of WPRE sequences treatment increased ZFN activity for all ZFNs tested.

Figure 2:
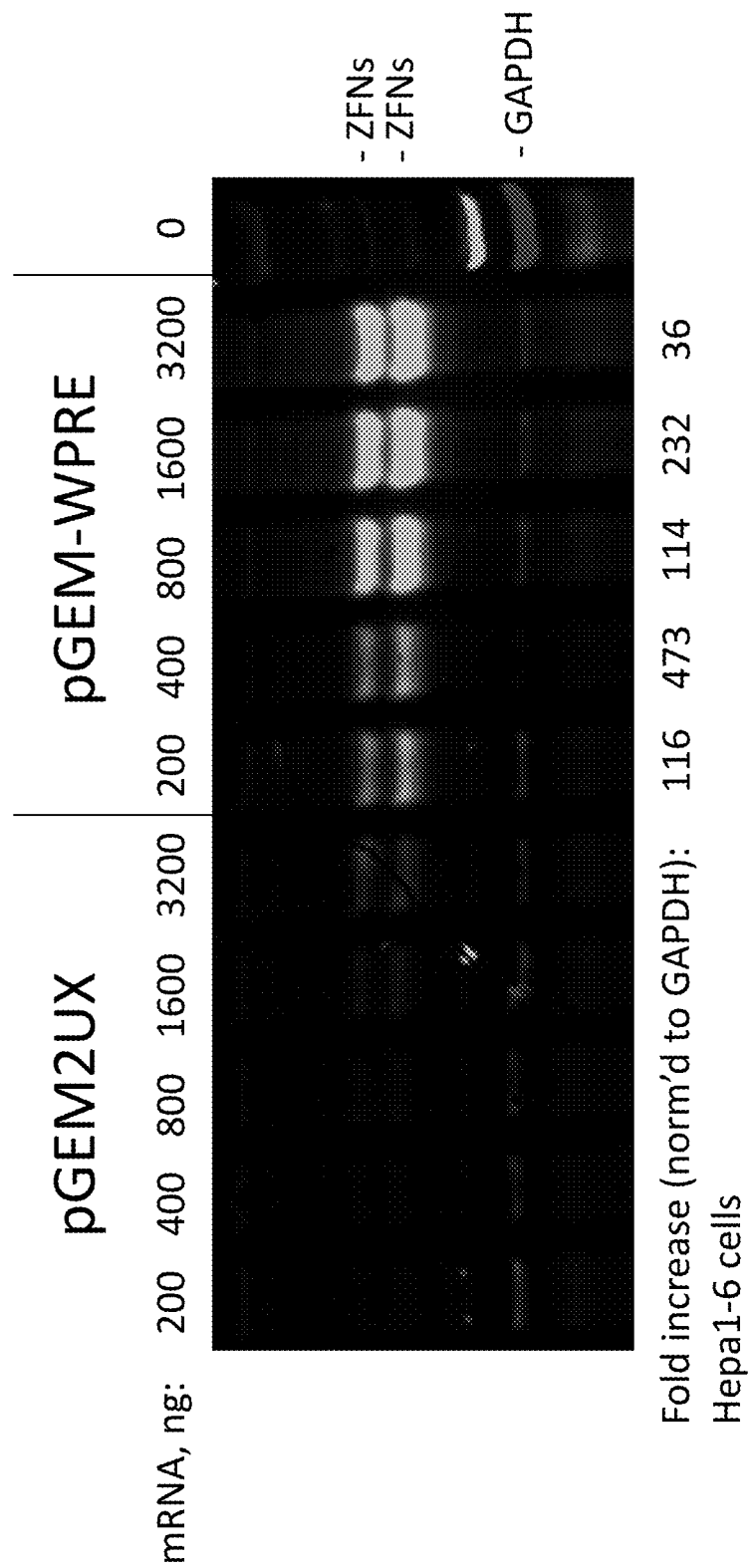
FIG. 2 depicts a Western blot showing how Hepa 1-6 cells transfected with mRNAs encoding the mouse albumin nucleases display increased expression of the nuclease in the presence of a WPRE J04514 3' UTR.
Figure 5:
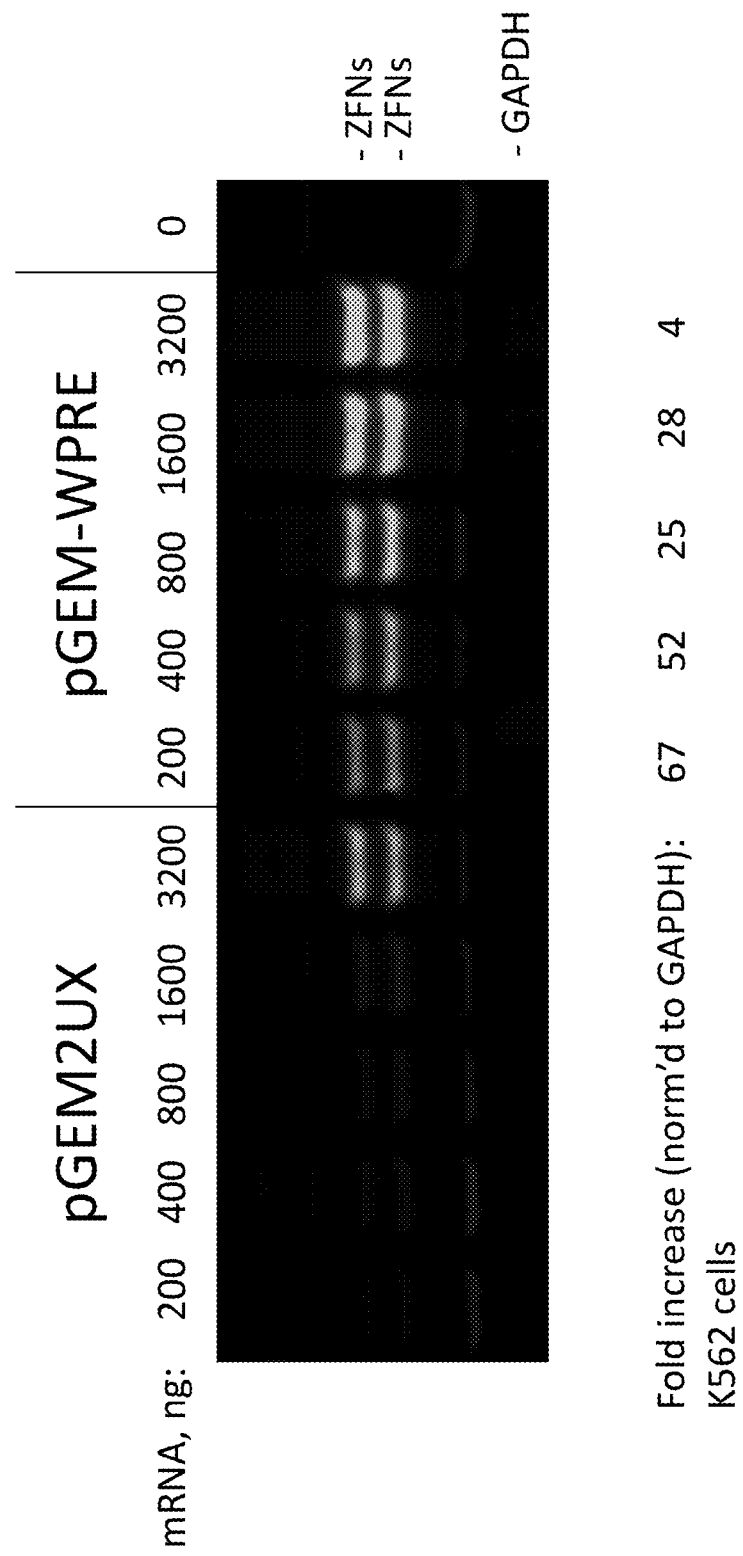
FIG. 5 depicts a Western blot showing how K562 cells transfected with mRNAs encoding the human CCR5-specific nucleases display increased nuclease expression in the presence of a WPRE J04514 3' UTR.
Figure 6:
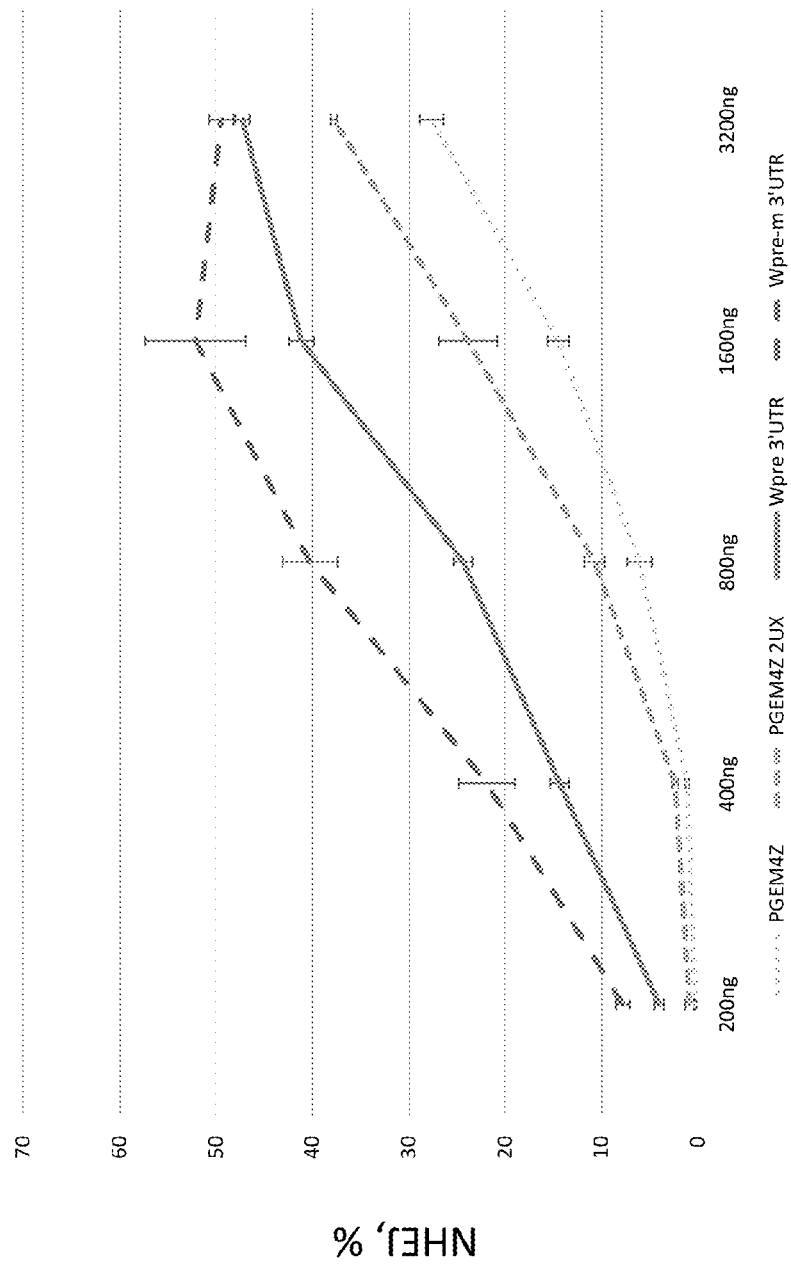
FIG. 6 depicts WPRE J04514 and WPRE-m J02442 3' UTR enhancement of CCR5 nuclease-mediated NHEJ in CD34+ hematopoietic stem and progenitor cells (HSPCs). Cells transfected with mRNAs encoding the nucleases and either WPRE sequence show enhanced nuclease associated NHEJ as compared with mRNAs lacking the WPRE. WPRE J04514, solid line; WPRE-m J02442, long dashed line; pGEM4Z, dotted light grey line; pGEM4Z 2UX, grey short dashed line. Error bars indicate the standard deviations of biological triplicates.
Figure 7:
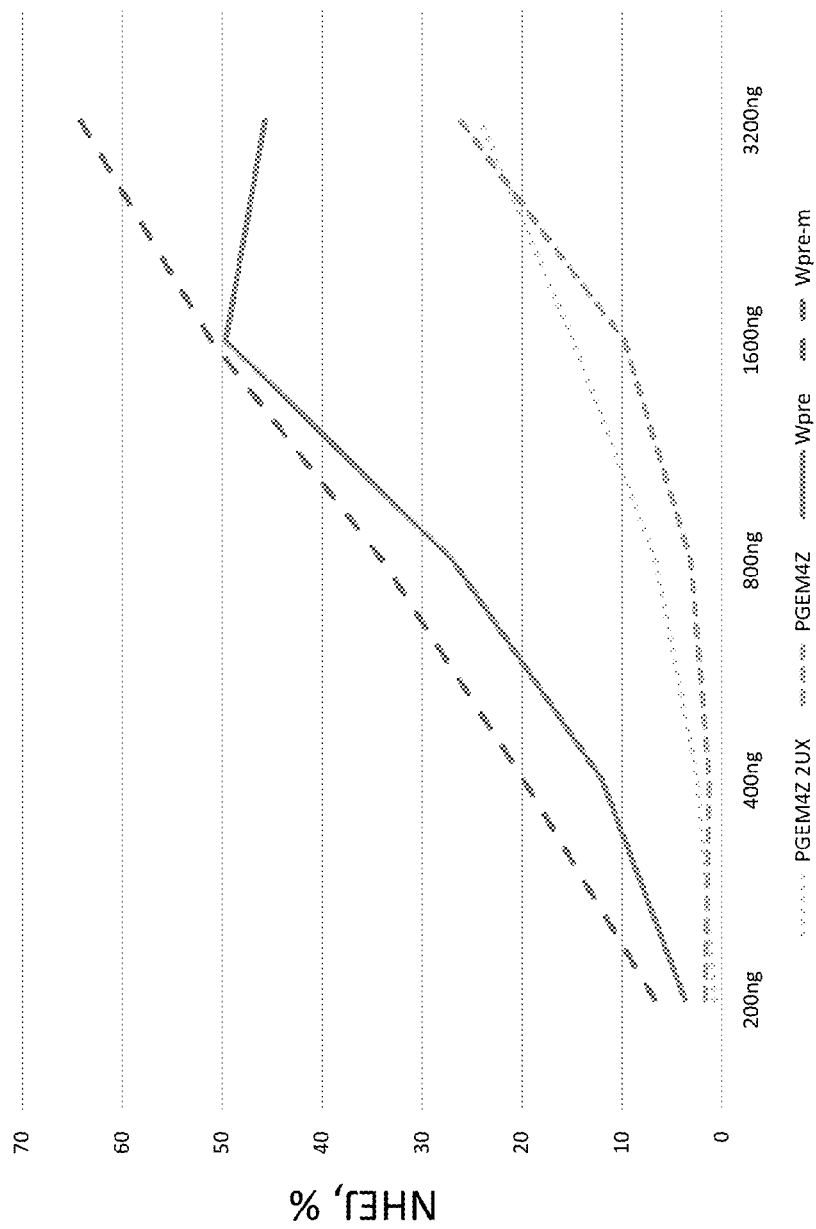
FIG. 7 depicts WPRE J04514 and WPRE-m J02442 3' UTR enhancement of CCR5 nuclease-mediated NHEJ in CD8+ T cells. Cells transfected with mRNAs encoding the nucleases and either WPRE sequence show enhanced nuclease associated NHEJ. WPRE J04514, solid line; WPRE-m J02442, long dashed line; pGEM4Z, dotted light grey line; pGEM4Z 2UX, grey short dashed line.
Figure 8:
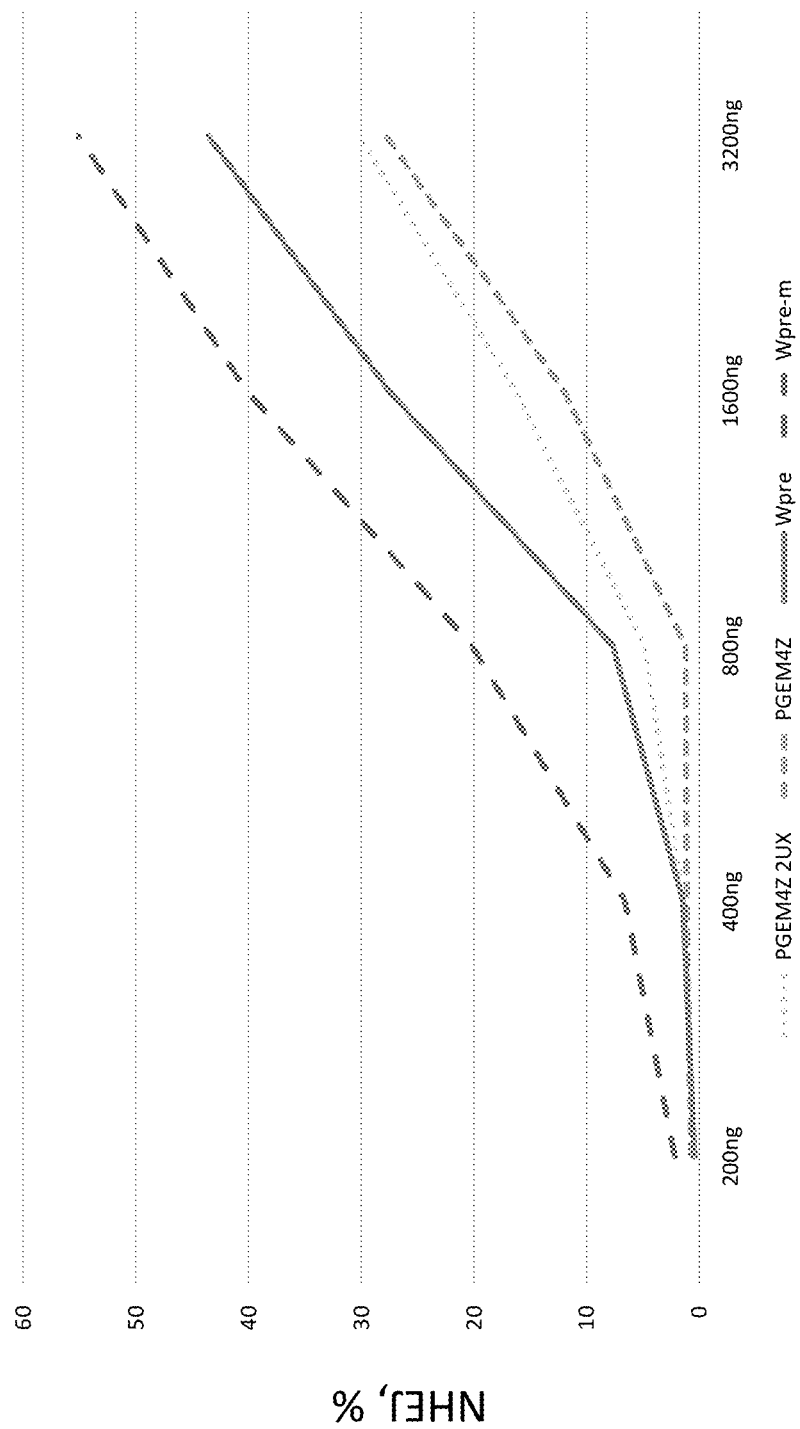
FIG. 8 depicts WPRE J04514 and WPRE-m J02442 3' UTRs enhancement of CCR5 nuclease-mediated NHEJ in CD4+ T cells. Cells transfected with mRNAs encoding the nucleases and either WPRE sequence show enhanced nuclease associated NHEJ. WPRE J04514, solid line; WPRE-m J02442, long dashed line; pGEM4Z, dotted light grey line; pGEM4Z 2UX, grey short dashed line.

In addition, ZFN protein level and activity with and without WPRE sequences was also determined. As show in FIGS. 2 and 5, the levels of ZFN protein were significantly increased when a WPRE sequence was included in the ZFN-encoding mRNA.

Thus, the presence of a WPRE sequence increased ZFN expression and ZFN activity (genome modification) both in vitro and in vivo.

Example 3: WPRE-Mediated Increase in the Frequency of Alleles Mutated by ZFN-Driven NHEJ is Enhanced by Cold-Shock Treatment To examine if the WPRE-mediated increase in ZFN activity was additive with the increase effected by hypothermic (cold shock) conditions (see, U.S. Pat. No. 8,772,008), CD34+ cells were transfected with ZFN mRNAs as described above and immediately following transfection, the cells were divided into two different flasks and incubated in a 5% $CO_2$ atmosphere at either 30° C. for 18 hours then at 37° C. for 54 hours or 37° C. for 72 hours.

Figure 9A:
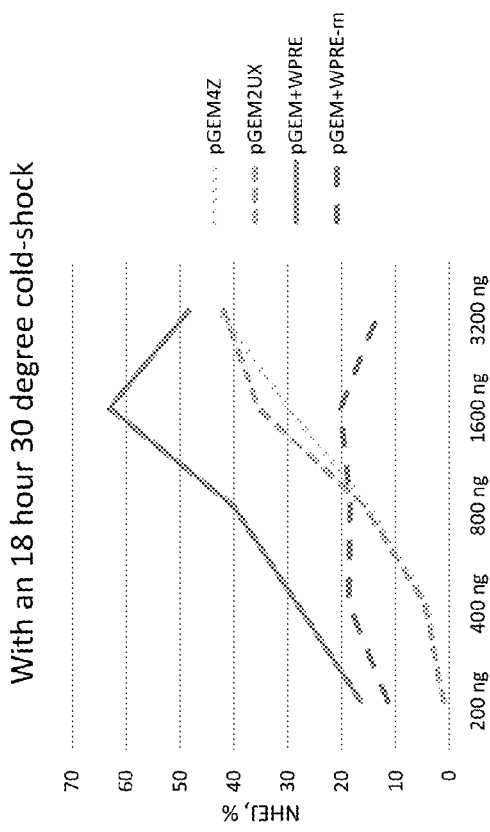
FIGS. 9A and 9B depict WPRE J04514 and WPRE-m J02442 3' UTR enhancement of CCR5 nuclease-mediated NHEJ in CD34+ HSPCs using the indicated mRNAs encoding the nucleases and optionally the indicated WPRE sequence, with (FIG. 9B) or without (FIG. 9A) hypothermic (cold) shock treatment.
Figure 9B:
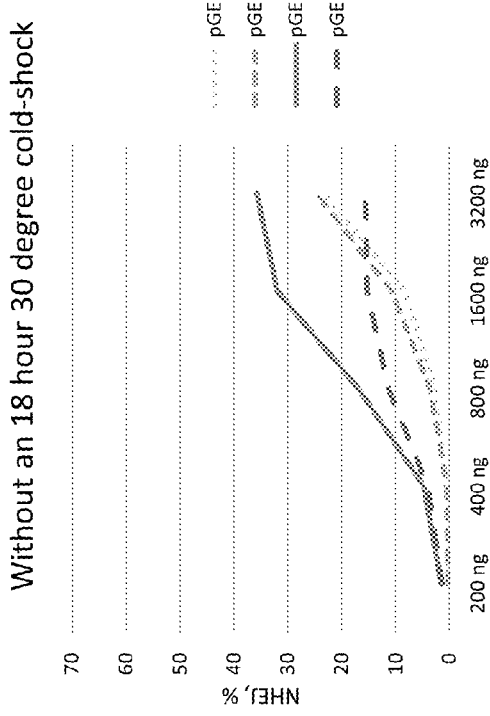
Figure 10B:
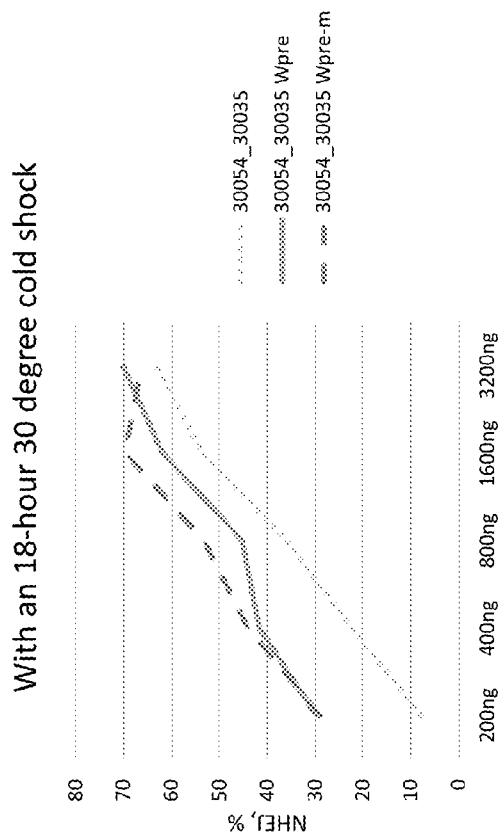
FIGS. 10A and 10B depict WPRE J04514 and WPRE-m J02442 3' UTR enhancement of AAVS1 nuclease-mediated NHEJ in CD34+ HSPCs using the indicated mRNAs encoding the nucleases and optionally the indicated WPRE sequence, with (FIG. 10B) or without (FIG. 10A) hypothermic (cold) shock treatment.
Figure 10A:
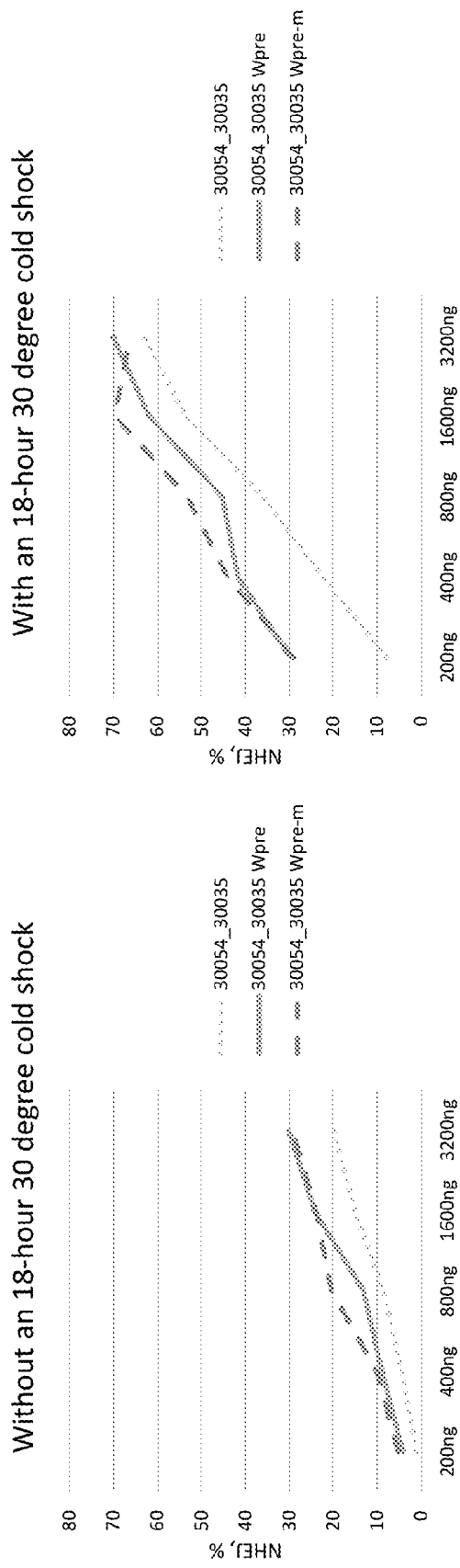
Figure 11A:
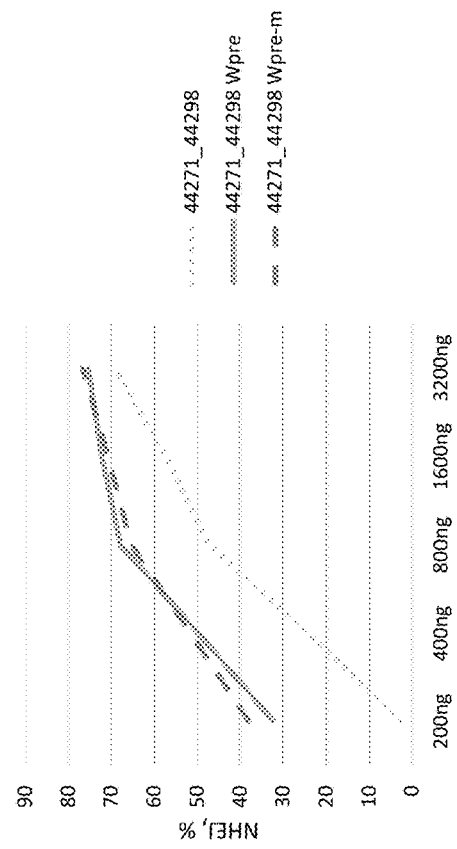
FIGS. 11A and 11B depict WPRE J04514 and WPRE-m J02442 3' UTR enhancement of IL2Rγ nuclease-mediated NHEJ in CD34+ HSPCs using the indicated mRNAs encoding the nucleases and optionally the indicated WPRE sequence, with (FIG. 11B) or without (FIG. 11A) hypothermic (cold) shock treatment.
Figure 11B:
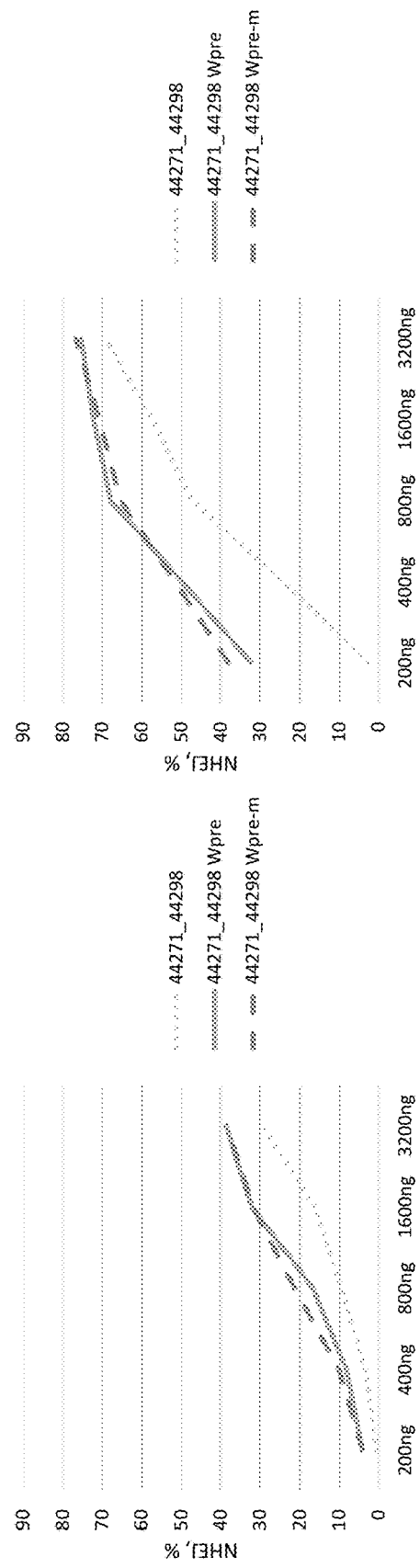
Figure 12A:
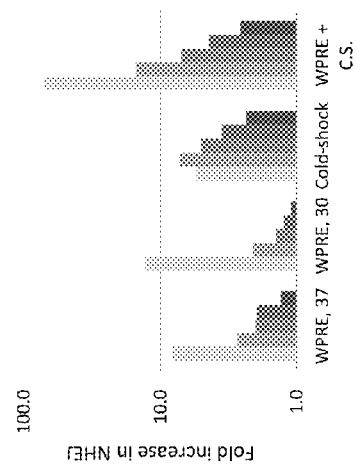
FIGS. 12A through 12C depict the isolated effects on nuclease activity in CD34+ cells from either WPRE inclusion in the mRNA, (both at 37° C. and with a 30° C. cold shock), cold shock alone, and the combination of a WPRE and cold shock treatment.
Figure 12B:
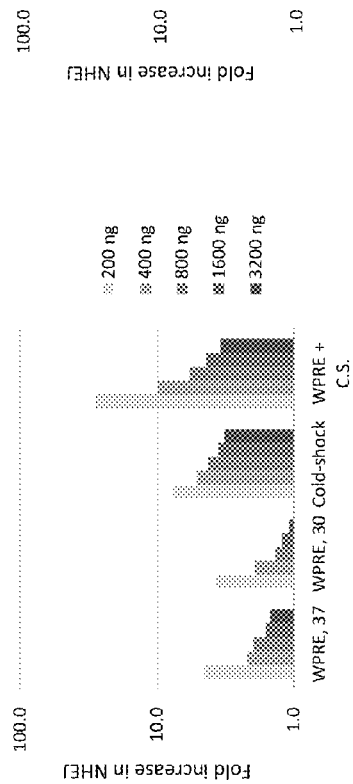
Figure 12C:
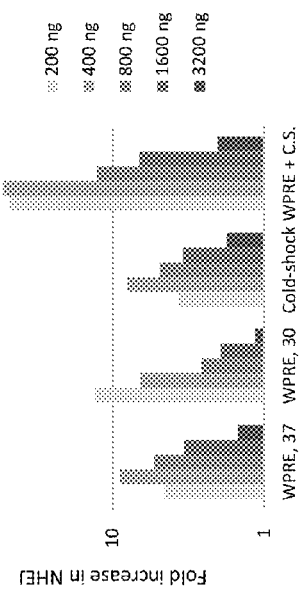

In all cases, NHEJ was further enhanced by cold-shock of WPRE as compared to cells without WPRE sequences. Exemplary results are shown in FIGS. 9 to 11. Results depicting the enhancement of cold show was shown using ZFNs in CD34+ cells (CCR5 targeted ZFNs, FIG. 9), (AAVS1-targeted ZFNs, FIG. 10), (ILR2γ-targeted ZFNs, FIG. 11). FIG. 12A-C delineates the increase in the NHEJ data in FIG. 9-11 that is specific to the indicated treatment (WPRE at 37° C., WPRE at 30° C., hypothermic shock alone, and a combination of the WPRE and hypothermic shock).

Thus, WPRE enhancement of nuclease activity is additive with the improvement obtained from hypothermic shock. Cold shock resulted in similar improvements in primary cells as well as transformed lines derived from a variety of species, independent of the ZFN pair or delivery method.

Example 4: WPRE Mediates an Increase in the Frequency of Alleles Mutated by TALE Nuclease-Driven NHEJ To determine if inclusion of a WPRE element in the 3' UTR of a TALE nuclease mRNA transcript could increase TALE nuclease activity, we transfected CCR5-specific TALE nucleases either with or without the inclusion of a J04514 WPRE or the mutant version of the J02442 WPRE into CD34+ cells as described above. Genomic DNA was harvested and mutagenic NHEJ activity was assayed as described as above.

Figures 13A, 13B:
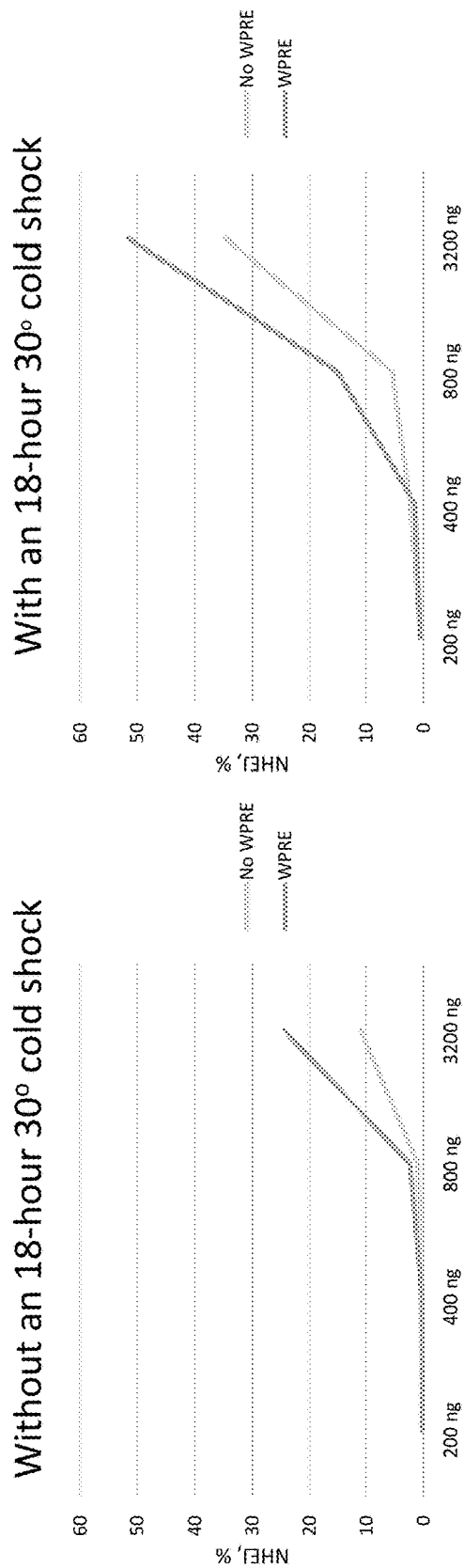
FIGS. 13A and 13B depict WPRE J04514 3' UTRs enhancement of CCR5 TALE nuclease-mediated NHEJ mediated in CD34+ HSPCs using the indicated mRNAs encoding the nucleases and optionally the indicated WPRE sequence, with (FIG. 13B) or without (FIG. 13A) hypothermic (cold) shock treatment.

The resulting data are displayed in FIGS. 13A-B and indicate that inclusion of a WPRE sequence increases the frequency of mutated alleles generated by TALE nuclease treatment.

Example 5: WPRE-Mediates an Increase in the Frequency of Alleles Mutated by CRISPR/Cas-Driven NHEJ To determine if inclusion of a WPRE element in the 3' UTR of a Cas9 mRNA transcript could increase CRISPR-Cas9/guide RNA nuclease activity, CD34+ HSPCs are transfected with a varying amount of Cas9 nuclease mRNA (either with or without the inclusion of a J04514 WPRE) along with a constant amount of a plasmid designed to target Cas9 nuclease activity to the AAVS1 locus. Genomic DNA is harvested and mutagenic NHEJ activity is assayed as described as above.

The resulting data indicates that inclusion of a WPRE sequence increases the frequency of mutated alleles generated by CRISPR-Cas9/guide RNA nuclease treatment.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of increasing nuclease activity in a cell, the method comprising: introducing an mRNA comprising a 3' untranslated region (3' UTR) and encoding at least one component of one or more nucleases into the cell, wherein the mRNA comprises a woodchuck hepatitis virus posttranslational regulatory element (WPRE) as shown in any of SEQ ID NOs:1-3 in the 3' UTR.

2. The method of claim 1, wherein the WPRE is a wild-type WPRE.

3. The method of claim 1, wherein the nuclease is a zinc finger nuclease, a TALEN and/or a CRISPR/Cas and/or a Cfp1 CRISPR/Cas nuclease system.

4. The method of claim 1, further comprising subject the cells to cold-shock conditions.

5. An isolated mRNA comprising a WPRE sequence as shown in any of SEQ ID NO:1-3 in the 3' UTR and a sequence encoding at least one component of a nuclease or a transcription factor (TF).

6. The mRNA of claim 5, wherein the sequence encodes a nuclease.

7. The mRNA of claim 5, wherein the nuclease is a zinc finger nuclease, a TALEN and/or at least one component of a CRISPR/Cas nuclease system.

8. The mRNA of claim 5, wherein the Cas protein is a Cas and/or Cfp1 protein.

9. The mRNA of claim 5, wherein the sequence encodes a transcription factor.

10. The mRNA of claim 9, wherein the transcription factor is a ZF-TF, a TALE-TF or a CRISPR/Cas TF.

11. The mRNA of claim 5, further comprising a polyA sequence.

* * * * *

```
                              SEQUENCE LISTING

<160> NUMBER OF SEQ ID NOS: 4

<210> SEQ ID NO 1
<211> LENGTH: 592
<212> TYPE: DNA
<213> ORGANISM: Woodchuck hepatitis virus

<400> SEQUENCE: 1
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact     240 ggttggggca ttgccaccac ctgtcagctc ctttccggga ctttcgcttt cccctccct    300 attgccacgg cggaactcat cgccgcctgc cttgcccgct gctggacagg ggctcggctg    360
ttgggcactg acaattccgt ggtgttgtcg gggaagctga cgtcctttcc atggctgctc    420
gcctgtgttg ccacctggat tctgcgcggg acgtccttct gctacgtccc ttcggccctc    480
aatccagcgg accttcctte ccgcggcctg ctgccggctc tgcggcctct tccgcgtctt    540
cgccttcgcc ctcagacgag tcggatctcc ctttgggccg cctcccgcc tg             592

<210> SEQ ID NO 2
<211> LENGTH: 592
<212> TYPE: DNA
<213> ORGANISM: Woodchuck hepatitis virus

<400> SEQUENCE: 2
aatcaacctc tggattacaa aatttgtgaa agattgactg atattcttaa ctatgttgct      60
ccttttacgc tgtgtggata tgctgcttta atgcctctgt atcatgctat tgcttcccgt     120
acggctttcg ttttctcctc cttgtataaa tcctggttgc tgtctcttta tgaggagttg     180
tggcccgttg tccgtcaacg tggcgtggtg tgctctgtgt ttgctgacgc aaccccact    240 ggctggggca ttgccaccac ctgtcaactc ctttctggga ctttcgcttt cccctcccg    300 atcgccacgg cagaactcat cgccgcctgc cttgcccgct gctggacagg ggctaggttg    360
ctgggcactg ataattccgt ggtgttgtcg gggaagctga cgtcctttcc atggctgctc    420
gcctgtgttg ccaactggat cctgcgcggg acgtccttct gctacgtccc ttcggctctc    480
aatccagcgg acctcccttc ccgaggcctt ctgccggttc tgcggcctct cccgcgtctt    540
cgctttcggc ctccgacgag tcggatctcc ctttgggccg cctcccgcc tg             592

<210> SEQ ID NO 3
<211> LENGTH: 245
<212> TYPE: DNA
<213> ORGANISM: Woodchuck hepatitis virus

<400> SEQUENCE: 3
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttag ttcttgccac ggcggaactc    180
atcgccgcct gccttgcccg ctgctggaca ggggctcggc tgttgggcac tgacaattcc    240
gtggt                                                                245
```

```
<210> SEQ ID NO 4
<211> LENGTH: 9
<212> TYPE: PRT
<213> ORGANISM: Unknown
<220> FEATURE:
<223> OTHER INFORMATION: Description of Unknown: 'LAGLIDADG'
      family peptide motif sequence

<400> SEQUENCE: 4

Leu Ala Gly Leu Ile Asp Ala Asp Gly
1               5
```